(12) United States Patent
Kheradvar et al.

(10) Patent No.: US 11,666,444 B2
(45) Date of Patent: Jun. 6, 2023

(54) ATRIAL CAGE FOR PLACEMENT, SECURING AND ANCHORING OF ATRIOVENTRICULAR VALVES

(71) Applicant: The Regents of the University of California, Oakland, CA (US)

(72) Inventors: Arash Kheradvar, Irvine, CA (US); Gregory S. Kelley, Santee, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/636,170

(22) PCT Filed: Aug. 2, 2018

(86) PCT No.: PCT/US2018/045030
§ 371 (c)(1),
(2) Date: Feb. 3, 2020

(87) PCT Pub. No.: WO2019/028264
PCT Pub. Date: Feb. 7, 2019

(65) Prior Publication Data
US 2020/0368023 A1  Nov. 26, 2020

Related U.S. Application Data

(60) Provisional application No. 62/540,916, filed on Aug. 3, 2017.

(51) Int. Cl.
*A61F 2/24* (2006.01)

(52) U.S. Cl.
CPC .......... *A61F 2/2487* (2013.01); *A61F 2/2415* (2013.01); *A61F 2/2418* (2013.01);
(Continued)

(58) Field of Classification Search
CPC ....................................... A61F 2/24
See application file for complete search history.

(56) References Cited

U.S. PATENT DOCUMENTS

| 5,332,402 A | 7/1994 | Teitelbaum |
| 5,728,152 A | 3/1998 | Mirsch, II et al. |

(Continued)

OTHER PUBLICATIONS

PCT International Search Report and the Written Opinion of the International Searching Authority for PCT/US2018/045030 ; dated Oct. 23, 2018.

(Continued)

*Primary Examiner* — Jacqueline Woznicki
(74) *Attorney, Agent, or Firm* — Tope-McKay & Associates

(57) ABSTRACT

Described is a collapsible atrial cage for percutaneous delivery and implantation of an atrioventricular valve within an atrium of the heart. The atrial cage includes an atrial portion and a ventricular portion. The ventricular portion is attached with and separated from the atrial portion by a valve juncture portion. Notably, the cage includes at least one interlock shaped to lock with and secure an atrioventricular valve proximate the valve juncture portion. Thus, when deployed and expanded, the atrioventricular valve is secured at the atrioventricular juncture.

14 Claims, 25 Drawing Sheets

(52) U.S. Cl.
CPC ............... *A61F 2210/0014* (2013.01); *A61F 2220/0025* (2013.01)

(56) References Cited

U.S. PATENT DOCUMENTS

| | | | |
|---|---|---|---|
| 5,957,949 A | 9/1999 | Leonhardt et al. | |
| 6,454,799 B1 * | 9/2002 | Schreck | A61F 2/2469 623/2.14 |
| 6,485,489 B2 | 11/2002 | Teirstein et al. | |
| 6,656,221 B2 | 12/2003 | Taylor et al. | |
| 6,875,231 B2 | 4/2005 | Anduiza et al. | |
| 6,949,122 B2 | 8/2005 | Adams et al. | |
| 6,974,476 B2 | 12/2005 | McGuckin, Jr. et al. | |
| 7,175,656 B2 | 2/2007 | Khairkhahan | |
| 7,270,676 B2 | 8/2007 | Alferness et al. | |
| 7,445,632 B2 | 11/2008 | McGuckin, Jr. et al. | |
| 7,470,285 B2 | 12/2008 | Nugent et al. | |
| 7,500,989 B2 | 3/2009 | Solem et al. | |
| 7,621,948 B2 | 11/2009 | Herrmann et al. | |
| 7,632,308 B2 | 12/2009 | Loulmet | |
| 7,758,639 B2 | 7/2010 | Mathis | |
| 7,803,184 B2 | 9/2010 | McGuckin, Jr. et al. | |
| 7,967,853 B2 | 6/2011 | Eidenschink et al. | |
| 7,981,151 B2 | 7/2011 | Rowe | |
| 7,993,394 B2 | 8/2011 | Hariton et al. | |
| 8,070,800 B2 | 12/2011 | Lock et al. | |
| 8,070,802 B2 | 12/2011 | Lamphere et al. | |
| 8,092,524 B2 | 1/2012 | Nugent et al. | |
| 8,167,935 B2 | 5/2012 | McGuckin, Jr. et al. | |
| 8,236,049 B2 | 8/2012 | Rowe et al. | |
| 8,366,768 B2 | 2/2013 | Zhang | |
| 8,414,645 B2 | 4/2013 | Dwork et al. | |
| 8,449,599 B2 | 5/2013 | Chau et al. | |
| 8,454,685 B2 | 6/2013 | Hariton et al. | |
| 8,460,366 B2 | 6/2013 | Rowe | |
| 8,470,023 B2 | 6/2013 | Eidenschink et al. | |
| 8,579,964 B2 | 11/2013 | Lane et al. | |
| 8,852,272 B2 | 10/2014 | Gross et al. | |
| 8,926,691 B2 | 1/2015 | Chau et al. | |
| 8,926,694 B2 | 1/2015 | Costello | |
| 8,956,404 B2 | 2/2015 | Bortlein et al. | |
| 8,968,395 B2 | 3/2015 | Hauser et al. | |
| 8,979,922 B2 | 3/2015 | Jayasinghe et al. | |
| 8,986,373 B2 | 3/2015 | Chau et al. | |
| 8,992,604 B2 | 3/2015 | Gross et al. | |
| 8,998,979 B2 | 4/2015 | Seguin et al. | |
| 9,011,531 B2 | 4/2015 | Rourke et al. | |
| 9,017,399 B2 | 4/2015 | Gross et al. | |
| 9,023,098 B2 | 5/2015 | Kuehn | |
| 9,023,099 B2 | 5/2015 | Duffy et al. | |
| 9,034,032 B2 | 5/2015 | McLean et al. | |
| 9,034,033 B2 | 5/2015 | McLean et al. | |
| 9,039,757 B2 | 5/2015 | McLean et al. | |
| 9,060,856 B2 | 6/2015 | Seguin et al. | |
| 9,066,800 B2 | 6/2015 | Clague et al. | |
| 9,072,603 B2 | 7/2015 | Tuval et al. | |
| 9,084,676 B2 | 7/2015 | Chau et al. | |
| 9,119,713 B2 | 9/2015 | Board et al. | |
| 9,155,617 B2 | 10/2015 | Carpentier et al. | |
| 9,192,466 B2 | 11/2015 | Kovalsky et al. | |
| 9,241,790 B2 | 1/2016 | Lane et al. | |
| 9,248,014 B2 | 2/2016 | Lane et al. | |
| 9,283,072 B2 | 3/2016 | Bruchman et al. | |
| 9,295,547 B2 | 3/2016 | Costello et al. | |
| 9,295,552 B2 | 3/2016 | McLean et al. | |
| 9,308,087 B2 | 4/2016 | Lane et al. | |
| 9,314,556 B2 | 4/2016 | Tuseth | |
| 9,333,077 B2 | 5/2016 | Peter | |
| 9,358,108 B2 | 6/2016 | Bortlein et al. | |
| 9,375,312 B2 | 6/2016 | Weber | |
| 9,387,075 B2 | 7/2016 | Bortlein et al. | |
| 9,387,078 B2 | 7/2016 | Gross et al. | |
| 9,402,721 B2 | 8/2016 | Buchbinder et al. | |
| 9,421,083 B2 | 8/2016 | Eidenschink et al. | |
| 9,433,500 B2 | 9/2016 | Chau et al. | |
| 9,439,757 B2 | 9/2016 | Wallace et al. | |
| 9,439,763 B2 | 9/2016 | Geist et al. | |
| 9,492,273 B2 | 11/2016 | Wallace et al. | |
| 9,498,332 B2 | 11/2016 | Hacohen et al. | |
| 9,526,611 B2 | 12/2016 | Tegels et al. | |
| 9,526,612 B2 | 12/2016 | Board et al. | |
| 9,526,613 B2 | 12/2016 | Gross et al. | |
| 9,532,870 B2 | 1/2017 | Cooper et al. | |
| 9,539,378 B2 | 1/2017 | Tuseth | |
| 9,572,666 B2 | 2/2017 | Basude et al. | |
| 9,579,197 B2 * | 2/2017 | Duffy | A61F 2/2427 |
| 9,579,199 B2 | 2/2017 | Hauser et al. | |
| 9,610,156 B2 | 4/2017 | Lashinski | |
| 9,610,159 B2 | 4/2017 | Christianson et al. | |
| 9,622,862 B2 | 4/2017 | Lashinski et al. | |
| 9,655,722 B2 | 5/2017 | Morriss et al. | |
| 9,662,204 B2 | 5/2017 | Hariton et al. | |
| 9,662,206 B2 | 5/2017 | Bortlein et al. | |
| 9,675,454 B2 | 6/2017 | Vidlund et al. | |
| 9,687,343 B2 | 6/2017 | Bortlein et al. | |
| 9,713,529 B2 | 7/2017 | Lane et al. | |
| 9,717,591 B2 | 8/2017 | Chau et al. | |
| 9,730,794 B2 | 8/2017 | Carpentier et al. | |
| 9,744,036 B2 | 8/2017 | Duffy et al. | |
| 9,763,657 B2 | 9/2017 | Hacohen et al. | |
| 9,763,779 B2 | 9/2017 | Bortlein et al. | |
| 9,770,329 B2 | 9/2017 | Lane et al. | |
| 9,833,313 B2 | 12/2017 | Board et al. | |
| 9,839,511 B2 * | 12/2017 | Ma | A61F 2/2412 |
| 9,839,517 B2 | 12/2017 | Centola et al. | |
| 9,844,435 B2 | 12/2017 | Eidenschink | |
| 9,889,003 B2 | 2/2018 | Bortlein et al. | |
| 9,895,219 B2 | 2/2018 | Costello | |
| 9,901,443 B2 | 2/2018 | Morriss et al. | |
| 9,931,204 B2 | 4/2018 | Rothstein et al. | |
| 9,931,206 B2 | 4/2018 | Weber | |
| 9,962,258 B2 | 5/2018 | Seguin et al. | |
| 9,962,260 B2 | 5/2018 | Krans et al. | |
| 9,968,445 B2 | 5/2018 | Kheradvar | |
| 9,999,425 B2 | 6/2018 | Kovach | |
| 10,010,411 B2 | 7/2018 | Peter | |
| 10,010,414 B2 | 7/2018 | Cooper et al. | |
| 10,010,417 B2 | 7/2018 | Keidar | |
| 10,016,271 B2 | 7/2018 | Morriss et al. | |
| 10,028,831 B2 | 7/2018 | Morin et al. | |
| 10,052,199 B2 | 8/2018 | Spence et al. | |
| 10,052,201 B2 | 8/2018 | Zhang et al. | |
| 10,052,204 B2 | 8/2018 | McLean et al. | |
| 10,064,718 B2 | 9/2018 | Keidar | |
| 10,064,719 B2 | 9/2018 | Bortlein et al. | |
| 10,070,954 B2 | 9/2018 | Braido et al. | |
| 10,080,651 B2 | 9/2018 | Bortlein et al. | |
| 10,085,835 B2 | 10/2018 | Thambar et al. | |
| 10,085,836 B2 | 10/2018 | Carpentier et al. | |
| 10,111,748 B2 | 10/2018 | Chau et al. | |
| 10,143,552 B2 | 12/2018 | Wallace et al. | |
| 10,166,101 B2 | 1/2019 | Altieri et al. | |
| 10,172,710 B2 | 1/2019 | Drasler et al. | |
| 10,179,044 B2 | 1/2019 | Ratz et al. | |
| 10,188,514 B2 | 1/2019 | Nasr | |
| 10,195,026 B2 | 2/2019 | Karapetian et al. | |
| 10,195,027 B2 | 2/2019 | Nasr | |
| 10,201,419 B2 | 2/2019 | Vidlund et al. | |
| 10,213,298 B2 | 2/2019 | Thambar et al. | |
| 10,219,896 B2 | 3/2019 | Sandstrom et al. | |
| 10,219,900 B2 | 3/2019 | Vidlund et al. | |
| 10,226,333 B2 | 3/2019 | Al-Jilaihawi et al. | |
| 10,226,334 B2 | 3/2019 | Rowe et al. | |
| 10,226,344 B2 | 3/2019 | Eidenschink et al. | |
| 10,245,143 B2 | 4/2019 | Gross et al. | |
| 10,258,464 B2 | 4/2019 | Delaloye et al. | |
| 10,285,808 B2 | 5/2019 | Bruchman et al. | |
| 10,292,711 B2 | 5/2019 | Olson et al. | |
| 10,292,816 B2 | 5/2019 | Raanani et al. | |
| 10,292,817 B2 | 5/2019 | Hariton et al. | |
| 10,299,917 B2 | 5/2019 | Morriss et al. | |
| 10,299,921 B2 | 5/2019 | Dale et al. | |
| 10,299,926 B2 | 5/2019 | Morin et al. | |
| 10,299,927 B2 | 5/2019 | McLean et al. | |

(56) References Cited

U.S. PATENT DOCUMENTS

| | | |
|---|---|---|
| 10,321,988 B2 | 6/2019 | Gorman, III et al. |
| 10,321,995 B1 | 6/2019 | Christianson et al. |
| 10,327,894 B2 | 6/2019 | Vidlund et al. |
| 10,335,278 B2 | 7/2019 | McLean et al. |
| 10,342,661 B2 | 7/2019 | Carpentier et al. |
| 10,350,066 B2 | 7/2019 | Cooper et al. |
| 10,357,363 B2 | 7/2019 | Frisby |
| 10,368,990 B2 | 8/2019 | Noe et al. |
| 10,376,361 B2 | 8/2019 | Gross et al. |
| 10,376,363 B2 | 8/2019 | Quadri et al. |
| 10,390,943 B2 | 8/2019 | Hernandez |
| 10,398,549 B2 | 9/2019 | Krone |
| 10,405,976 B2 | 9/2019 | Christianson et al. |
| 10,413,407 B2 | 9/2019 | Hariton et al. |
| 10,426,611 B2 | 10/2019 | Hariton et al. |
| 10,433,953 B2 | 10/2019 | Wallace et al. |
| 10,433,956 B2 | 10/2019 | Fuval et al. |
| 10,433,960 B1 | 10/2019 | Sutherland et al. |
| 10,433,961 B2 * | 10/2019 | McLean ............... A61F 2/2409 |
| 10,441,416 B2 | 10/2019 | Oba et al. |
| 10,441,421 B2 | 10/2019 | Perszyk et al. |
| 10,441,423 B2 | 10/2019 | Hauser et al. |
| 10,449,041 B2 | 10/2019 | Modine |
| 10,449,042 B2 | 10/2019 | Lane et al. |
| 10,456,243 B2 | 10/2019 | Robertson et al. |
| 10,456,247 B2 | 10/2019 | Nasr |
| 10,456,277 B2 | 10/2019 | Quadri |
| 10,463,481 B2 | 11/2019 | Geist et al. |
| 10,463,483 B2 | 11/2019 | Lim et al. |
| 10,470,876 B2 | 11/2019 | Gurovich et al. |
| 10,470,881 B2 | 11/2019 | Noe et al. |
| 10,492,905 B2 | 12/2019 | Hariton et al. |
| 10,500,038 B1 | 12/2019 | Orlov et al. |
| 10,507,102 B2 | 12/2019 | Chau et al. |
| 10,512,456 B2 | 12/2019 | Hacohen et al. |
| 10,531,951 B2 | 1/2020 | Spargias |
| 10,537,422 B2 | 1/2020 | Lane et al. |
| 10,537,429 B2 | 1/2020 | Duffy et al. |
| 10,537,672 B2 | 1/2020 | Fuseth et al. |
| 11,000,000 B2 * | 5/2021 | Diedering ............... A61F 2/243 |
| 2002/0087173 A1 | 7/2002 | Alferness et al. |
| 2002/0115994 A1 | 8/2002 | Teirstein et al. |
| 2003/0023303 A1 * | 1/2003 | Palmaz ................. A61F 2/2418 |
| | | 623/2.18 |
| 2003/0083538 A1 | 5/2003 | Adams et al. |
| 2004/0044406 A1 * | 3/2004 | Woolfson ................ A61F 2/848 |
| | | 623/2.11 |
| 2004/0049266 A1 | 3/2004 | Anduiza et al. |
| 2004/0153147 A1 | 8/2004 | Mathis |
| 2004/0210307 A1 | 10/2004 | Khairkhakan |
| 2004/0225353 A1 | 11/2004 | McGuckin, Jr. et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0137690 A1 * | 6/2005 | Salahieh ............... A61F 2/2418 |
| | | 623/2.11 |
| 2005/0165477 A1 | 7/2005 | Anduiza et al. |
| 2005/0234546 A1 | 10/2005 | Nugent et al. |
| 2006/0009841 A1 | 1/2006 | McGuckin et al. |
| 2006/0276874 A1 * | 12/2006 | Wilson ................ A61F 2/2475 |
| | | 623/1.13 |
| 2006/0287717 A1 | 12/2006 | Rowe et al. |
| 2006/0287719 A1 * | 12/2006 | Rowe .................. A61F 2/2409 |
| | | 623/2.18 |
| 2007/0016286 A1 | 1/2007 | Herrmann et al. |
| 2007/0043435 A1 * | 2/2007 | Seguin ................. A61F 2/2436 |
| | | 623/2.11 |
| 2007/0135912 A1 | 6/2007 | Mathis |
| 2007/0156233 A1 * | 7/2007 | Kapadia ................ A61F 2/2418 |
| | | 623/2.11 |
| 2007/0168024 A1 | 7/2007 | Khairkhahan |
| 2007/0203503 A1 * | 8/2007 | Salahieh ............... A61F 2/2427 |
| | | 623/2.11 |
| 2007/0213813 A1 | 9/2007 | Von Segesser et al. |
| 2007/0265702 A1 | 11/2007 | Lattouf |
| 2008/0091191 A1 | 4/2008 | Witzel et al. |
| 2008/0221672 A1 | 9/2008 | Lamphere et al. |
| 2008/0243245 A1 | 10/2008 | Thambar et al. |
| 2008/0275540 A1 * | 11/2008 | Wen .................... A61F 2/2418 |
| | | 623/1.26 |
| 2008/0300678 A1 | 12/2008 | Eidenschink et al. |
| 2008/0319526 A1 | 12/2008 | Hill et al. |
| 2009/0030503 A1 | 1/2009 | Ho |
| 2009/0030510 A1 | 1/2009 | Ho |
| 2009/0054974 A1 | 2/2009 | McGuckin, Jr. et al. |
| 2009/0082858 A1 | 3/2009 | Nugent et al. |
| 2009/0198315 A1 * | 8/2009 | Boudjemline ........... D04C 3/48 |
| | | 623/1.2 |
| 2009/0222082 A1 | 9/2009 | Lock et al. |
| 2009/0259306 A1 | 10/2009 | Rowe |
| 2009/0276040 A1 * | 11/2009 | Rowe .................... A61F 2/90 |
| | | 623/2.18 |
| 2010/0036479 A1 * | 2/2010 | Hill .................... A61F 2/2418 |
| | | 623/1.15 |
| 2010/0042208 A1 | 2/2010 | Herrmann et al. |
| 2010/0049306 A1 | 2/2010 | House et al. |
| 2010/0049313 A1 * | 2/2010 | Alon .................... A61F 2/2439 |
| | | 623/2.11 |
| 2010/0161036 A1 * | 6/2010 | Pintor ................... A61F 2/2433 |
| | | 623/2.11 |
| 2010/0204785 A1 | 8/2010 | Alkhatib |
| 2010/0217382 A1 | 8/2010 | Chau et al. |
| 2010/0249917 A1 | 9/2010 | Zhang |
| 2010/0249918 A1 | 9/2010 | Zhang |
| 2010/0280602 A1 | 11/2010 | Mathis |
| 2010/0331972 A1 * | 12/2010 | Pintor ................... A61F 2/2433 |
| | | 623/2.11 |
| 2011/0004300 A1 | 1/2011 | McGuckin, Jr. et al. |
| 2011/0112632 A1 | 5/2011 | Chau et al. |
| 2011/0137397 A1 | 6/2011 | Chau et al. |
| 2011/0208297 A1 * | 8/2011 | Tuval ................... A61F 2/2418 |
| | | 623/2.17 |
| 2011/0251678 A1 | 10/2011 | Eidenschink et al. |
| 2011/0319988 A1 | 12/2011 | Schankereli et al. |
| 2011/0319989 A1 | 12/2011 | Lane et al. |
| 2012/0016470 A1 | 1/2012 | Rowe |
| 2012/0022639 A1 * | 1/2012 | Hacohen ............... A61F 2/2439 |
| | | 623/2.11 |
| 2012/0022640 A1 | 1/2012 | Gross et al. |
| 2012/0059458 A1 * | 3/2012 | Buchbinder .......... A61F 2/2409 |
| | | 623/2.36 |
| 2012/0101572 A1 | 4/2012 | Kovalsky et al. |
| 2012/0179244 A1 | 7/2012 | Schankereli et al. |
| 2012/0203333 A1 | 8/2012 | McGuckin, Jr. et al. |
| 2012/0290082 A1 | 11/2012 | Quint et al. |
| 2013/0035759 A1 | 2/2013 | Gross et al. |
| 2013/0053950 A1 | 2/2013 | Rowe et al. |
| 2013/0116779 A1 | 5/2013 | Weber |
| 2013/0172992 A1 | 7/2013 | Gross et al. |
| 2013/0184811 A1 | 7/2013 | Rowe et al. |
| 2013/0190861 A1 | 7/2013 | Chau et al. |
| 2013/0211508 A1 | 8/2013 | Lane et al. |
| 2013/0261737 A1 | 10/2013 | Costello |
| 2013/0261738 A1 | 10/2013 | Clague et al. |
| 2013/0282101 A1 | 10/2013 | Eidenschink et al. |
| 2013/0304197 A1 * | 11/2013 | Buchbinder .......... A61F 2/2418 |
| | | 623/2.11 |
| 2013/0304200 A1 * | 11/2013 | McLean ............... A61F 2/2436 |
| | | 623/2.18 |
| 2013/0310917 A1 * | 11/2013 | Richter ................. A61F 2/2412 |
| | | 623/1.12 |
| 2013/0310928 A1 * | 11/2013 | Morriss ................ A61F 2/2445 |
| | | 623/2.12 |
| 2013/0317598 A1 * | 11/2013 | Rowe .................... A61F 2/90 |
| | | 623/1.26 |
| 2013/0325114 A1 * | 12/2013 | McLean ............... A61F 2/2409 |
| | | 623/2.12 |
| 2014/0005778 A1 * | 1/2014 | Buchbinder .......... A61F 2/2412 |
| | | 623/2.18 |
| 2014/0012372 A1 * | 1/2014 | Chau .................... A61F 2/24 |
| | | 623/2.18 |
| 2014/0012373 A1 | 1/2014 | Chau et al. |

(56) References Cited

U.S. PATENT DOCUMENTS

| | | |
|---|---|---|
| 2014/0039611 A1 | 2/2014 | Lane et al. |
| 2014/0039613 A1* | 2/2014 | Navia .................... A61F 2/2412 623/2.18 |
| 2014/0046426 A1 | 2/2014 | Kovalsky |
| 2014/0088696 A1* | 3/2014 | Figulla .................. A61F 2/2418 623/2.17 |
| 2014/0128969 A1 | 5/2014 | Hill et al. |
| 2014/0148898 A1 | 5/2014 | Gross et al. |
| 2014/0163652 A1 | 6/2014 | Witzel et al. |
| 2014/0163672 A1 | 6/2014 | Seguin et al. |
| 2014/0172083 A1* | 6/2014 | Bruchman ............. A61F 2/2433 623/2.17 |
| 2014/0180401 A1* | 6/2014 | Quill ...................... A61F 2/2418 623/2.17 |
| 2014/0194978 A1 | 7/2014 | Seguin et al. |
| 2014/0194979 A1 | 7/2014 | Seguin et al. |
| 2014/0194982 A1* | 7/2014 | Kovalsky .............. A61F 2/2412 623/2.38 |
| 2014/0194983 A1* | 7/2014 | Kovalsky .............. A61F 2/2445 623/2.38 |
| 2014/0214157 A1 | 7/2014 | Bortlein et al. |
| 2014/0222136 A1* | 8/2014 | Geist .................... A61F 2/2436 623/2.11 |
| 2014/0222142 A1* | 8/2014 | Kovalsky .............. A61F 2/2436 623/2.17 |
| 2014/0228946 A1 | 8/2014 | Chau et al. |
| 2014/0236287 A1 | 8/2014 | Clague et al. |
| 2014/0243954 A1 | 8/2014 | Shannon |
| 2014/0249621 A1 | 9/2014 | Eidenschink |
| 2014/0257466 A1 | 9/2014 | Board et al. |
| 2014/0257475 A1* | 9/2014 | Gross .................... A61F 2/2409 623/2.38 |
| 2014/0276971 A1 | 9/2014 | Kovach |
| 2014/0277388 A1* | 9/2014 | Skemp .................. A61F 2/2418 623/1.26 |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1* | 9/2014 | Bortlein ................ A61F 2/2418 623/2.11 |
| 2014/0296969 A1* | 10/2014 | Tegels ................... A61F 2/2412 623/2.11 |
| 2014/0296971 A1 | 10/2014 | Tegels et al. |
| 2014/0296972 A1 | 10/2014 | Tegels et al. |
| 2014/0296975 A1* | 10/2014 | Tegels ...................... A61F 2/07 623/2.18 |
| 2014/0309727 A1 | 10/2014 | Lamelas et al. |
| 2014/0316516 A1 | 10/2014 | Vidlund et al. |
| 2014/0324164 A1 | 10/2014 | Gross et al. |
| 2014/0350669 A1 | 11/2014 | Gillespie et al. |
| 2014/0358222 A1 | 12/2014 | Gorman, III et al. |
| 2014/0358224 A1* | 12/2014 | Tegels ................... A61F 2/2418 623/2.14 |
| 2014/0371844 A1 | 12/2014 | Dale et al. |
| 2015/0018943 A1 | 1/2015 | Paniagua et al. |
| 2015/0039081 A1* | 2/2015 | Costello ................ A61F 2/2436 623/2.11 |
| 2015/0045881 A1* | 2/2015 | Lim ...................... A61F 2/2418 623/2.38 |
| 2015/0119974 A1 | 4/2015 | Rothstein |
| 2015/0119978 A1 | 4/2015 | Tegels et al. |
| 2015/0127096 A1 | 5/2015 | Rowe et al. |
| 2015/0134057 A1 | 5/2015 | Rourke et al. |
| 2015/0142100 A1* | 5/2015 | Morriss ................. A61F 2/2445 623/2.4 |
| 2015/0142103 A1* | 5/2015 | Vidlund ................ A61F 2/2439 623/2.17 |
| 2015/0157458 A1 | 6/2015 | Thambar et al. |
| 2015/0164640 A1 | 6/2015 | McLean et al. |
| 2015/0173897 A1* | 6/2015 | Raanani .................. A61F 2/243 623/2.11 |
| 2015/0173898 A1 | 6/2015 | Drasler et al. |
| 2015/0173900 A1 | 6/2015 | Hauser et al. |
| 2015/0196390 A1* | 7/2015 | Ma ........................ A61F 2/2418 623/2.17 |
| 2015/0196393 A1 | 7/2015 | Vidlund et al. |
| 2015/0202044 A1 | 7/2015 | Chau et al. |
| 2015/0216655 A1 | 8/2015 | Lane et al. |
| 2015/0216661 A1 | 8/2015 | Hacohen et al. |
| 2015/0238312 A1 | 8/2015 | Lashinski |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257880 A1 | 9/2015 | Bortlein et al. |
| 2015/0257881 A1 | 9/2015 | Bortlein et al. |
| 2015/0257882 A1* | 9/2015 | Bortlein ................ A61F 2/2418 623/2.11 |
| 2015/0258260 A1 | 9/2015 | Tuseth |
| 2015/0258312 A1 | 9/2015 | Tuseth |
| 2015/0272586 A1 | 10/2015 | Herman et al. |
| 2015/0272737 A1 | 10/2015 | Dale et al. |
| 2015/0305860 A1* | 10/2015 | Wang ...................... A61L 27/20 623/2.17 |
| 2015/0320553 A1 | 11/2015 | Chau et al. |
| 2015/0327995 A1 | 11/2015 | Morin et al. |
| 2015/0327999 A1 | 11/2015 | Board et al. |
| 2015/0328000 A1 | 11/2015 | Ratz et al. |
| 2015/0328001 A1 | 11/2015 | McLean et al. |
| 2015/0328002 A1 | 11/2015 | McLean et al. |
| 2015/0335424 A1 | 11/2015 | McLean et al. |
| 2015/0335429 A1 | 11/2015 | Morriss et al. |
| 2015/0351903 A1* | 12/2015 | Morriss ................. A61F 2/2418 623/2.11 |
| 2015/0351904 A1 | 12/2015 | Cooper et al. |
| 2016/0015514 A1 | 1/2016 | Lashinski et al. |
| 2016/0022417 A1 | 1/2016 | Karapetian et al. |
| 2016/0038283 A1 | 2/2016 | Divekar et al. |
| 2016/0067039 A1 | 3/2016 | Rourke et al. |
| 2016/0089235 A1 | 3/2016 | Yellin |
| 2016/0089238 A1 | 3/2016 | Centola et al. |
| 2016/0106537 A1* | 4/2016 | Christianson ......... A61F 2/2448 623/2.17 |
| 2016/0120643 A1* | 5/2016 | Kupumbati ........... A61F 2/2436 623/2.18 |
| 2016/0143730 A1 | 5/2016 | Kheradvar |
| 2016/0157999 A1 | 6/2016 | Lane et al. |
| 2016/0199178 A1 | 7/2016 | Venkatasubramanian et al. |
| 2016/0199180 A1 | 7/2016 | Zeng et al. |
| 2016/0206424 A1 | 7/2016 | Al-Jilaihawi et al. |
| 2016/0242901 A1* | 8/2016 | Keren ................... A61F 2/2418 |
| 2016/0242905 A1* | 8/2016 | Chambers ............. A61F 2/2418 |
| 2016/0256272 A1 | 9/2016 | Weber |
| 2016/0262881 A1 | 9/2016 | Schankereli et al. |
| 2016/0302918 A1 | 10/2016 | Keidar |
| 2016/0302920 A1 | 10/2016 | Al-Jilaihawi |
| 2016/0302922 A1 | 10/2016 | Keidar |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324635 A1 | 11/2016 | Vidlund et al. |
| 2016/0331534 A1 | 11/2016 | Buchbinder et al. |
| 2016/0338826 A1 | 11/2016 | Chau et al. |
| 2016/0346084 A1 | 12/2016 | Taylor et al. |
| 2016/0367364 A1 | 12/2016 | Torrianni et al. |
| 2017/0014561 A1 | 1/2017 | Tuseth |
| 2017/0020695 A1 | 1/2017 | Quadri |
| 2017/0049564 A1 | 2/2017 | Board et al. |
| 2017/0056171 A1 | 3/2017 | Cooper et al. |
| 2017/0056176 A1 | 3/2017 | Rowe et al. |
| 2017/0057169 A1 | 3/2017 | Grbic et al. |
| 2017/0079790 A1 | 3/2017 | Vidlund et al. |
| 2017/0086973 A1 | 3/2017 | Zeng et al. |
| 2017/0095328 A1 | 4/2017 | Cooper et al. |
| 2017/0100236 A1* | 4/2017 | Robertson ............. A61F 2/2409 |
| 2017/0128199 A1 | 5/2017 | Gurovich et al. |
| 2017/0128203 A1 | 5/2017 | Zhang et al. |
| 2017/0143482 A1 | 5/2017 | Kveen et al. |
| 2017/0143486 A1 | 5/2017 | Zeng et al. |
| 2017/0143488 A1 | 5/2017 | Lashinski |
| 2017/0143489 A1 | 5/2017 | Lashinski |
| 2017/0165055 A1 | 6/2017 | Hauser et al. |

(56) References Cited

U.S. PATENT DOCUMENTS

| | | |
|---|---|---|
| 2017/0165058 A1 | 6/2017 | Rothstein et al. |
| 2017/0165069 A1 | 6/2017 | Eidenschink et al. |
| 2017/0189179 A1 | 7/2017 | Ratz et al. |
| 2017/0196688 A1 | 7/2017 | Christianson et al. |
| 2017/0209261 A1 | 7/2017 | Bortlein et al. |
| 2017/0209264 A1 | 7/2017 | Chau et al. |
| 2017/0216026 A1* | 8/2017 | Quill ............... A61F 2/2418 |
| 2017/0231759 A1 | 8/2017 | Geist et al. |
| 2017/0231763 A1 | 8/2017 | Yellin |
| 2017/0252153 A1 | 9/2017 | Chau et al. |
| 2017/0265994 A1 | 9/2017 | Krone |
| 2017/0265998 A1 | 9/2017 | Sandstrom et al. |
| 2017/0266003 A1* | 9/2017 | Hammer ............ A61F 2/2418 |
| 2017/0281336 A1 | 10/2017 | Lane et al. |
| 2017/0296339 A1 | 10/2017 | Thambar et al. |
| 2017/0325954 A1 | 11/2017 | Perszyk |
| 2017/0333186 A1 | 11/2017 | Spargias |
| 2017/0348098 A1 | 12/2017 | Rowe et al. |
| 2017/0348100 A1 | 12/2017 | Lane et al. |
| 2017/0354498 A1 | 12/2017 | Frisby |
| 2017/0360426 A1 | 12/2017 | Hacohen et al. |
| 2017/0360558 A1* | 12/2017 | Ma ................... A61F 2/2409 |
| 2018/0042719 A1* | 2/2018 | Chambers .......... A61F 2/2442 |
| 2018/0042721 A1* | 2/2018 | Chambers .............. A61F 2/24 |
| 2018/0049868 A1 | 2/2018 | Board et al. |
| 2018/0049873 A1 | 2/2018 | Manash et al. |
| 2018/0078365 A1 | 3/2018 | Zhang et al. |
| 2018/0085218 A1 | 3/2018 | Eidenschink |
| 2018/0098847 A1 | 4/2018 | Tuseth et al. |
| 2018/0099078 A1 | 4/2018 | Tuseth et al. |
| 2018/0125647 A1 | 5/2018 | Nasr |
| 2018/0125649 A1 | 5/2018 | Nasr |
| 2018/0125650 A1 | 5/2018 | Nasr |
| 2018/0125651 A1 | 5/2018 | Nasr |
| 2018/0153685 A1 | 6/2018 | Costello |
| 2018/0153695 A1 | 6/2018 | Cunningham et al. |
| 2018/0161156 A1 | 6/2018 | Nasr |
| 2018/0193140 A1 | 7/2018 | Weber |
| 2018/0200049 A1* | 7/2018 | Chambers .......... A61F 2/2436 |
| 2018/0206983 A1* | 7/2018 | Noe ................... A61F 2/2445 |
| 2018/0206988 A1* | 7/2018 | Chambers .......... A61F 2/2418 |
| 2018/0206989 A1 | 7/2018 | O'Connell et al. |
| 2018/0214264 A1 | 8/2018 | Rothstein et al. |
| 2018/0242976 A1 | 8/2018 | Kizuka |
| 2018/0243090 A1 | 8/2018 | Morin et al. |
| 2018/0250128 A1 | 9/2018 | Moore |
| 2018/0256321 A1 | 9/2018 | Zhang et al. |
| 2018/0256322 A1 | 9/2018 | Zhang et al. |
| 2018/0256327 A1 | 9/2018 | Perszyk et al. |
| 2018/0256329 A1* | 9/2018 | Chambers .......... A61F 2/2412 |
| 2018/0263767 A1 | 9/2018 | Chau et al. |
| 2018/0263768 A1 | 9/2018 | Zhang et al. |
| 2018/0263795 A1 | 9/2018 | Quadri |
| 2018/0296336 A1 | 10/2018 | Cooper et al. |
| 2018/0296341 A1* | 10/2018 | Noe ................... A61F 2/2412 |
| 2018/0311037 A1 | 11/2018 | Morriss et al. |
| 2018/0325662 A1* | 11/2018 | Modine .............. A61F 2/2418 |
| 2018/0344455 A1 | 12/2018 | Hacohen et al. |
| 2018/0344457 A1 | 12/2018 | Gross et al. |
| 2018/0368977 A1 | 12/2018 | Gorman, III et al. |
| 2019/0000616 A1 | 1/2019 | Zeng et al. |
| 2019/0029815 A1 | 1/2019 | Karrowni |
| 2019/0060060 A1 | 2/2019 | Chau et al. |
| 2019/0060071 A1 | 2/2019 | Lane et al. |
| 2019/0091016 A1 | 3/2019 | Kveen et al. |
| 2019/0125534 A1 | 5/2019 | Arcaro et al. |
| 2019/0125535 A1 | 5/2019 | Drasler et al. |
| 2019/0133761 A1 | 5/2019 | Rowe et al. |
| 2019/0142582 A1 | 5/2019 | Drasler et al. |
| 2019/0142585 A1 | 5/2019 | Ratz et al. |
| 2019/0159896 A1 | 5/2019 | Thambar et al. |
| 2019/0167421 A1 | 6/2019 | Chau et al. |
| 2019/0183639 A1 | 6/2019 | Moore |
| 2019/0201192 A1* | 7/2019 | Kruse ................. A61F 2/246 |
| 2019/0201193 A1 | 7/2019 | Delaloye et al. |
| 2019/0201197 A9 | 7/2019 | Lashinski |
| 2019/0247186 A1 | 8/2019 | Vidlund et al. |
| 2019/0247189 A1 | 8/2019 | Dale et al. |
| 2019/0247191 A1* | 8/2019 | Chambers .......... A61F 2/2454 |
| 2019/0262129 A1 | 8/2019 | Cooper et al. |
| 2019/0269512 A9 | 9/2019 | Lashinski |
| 2019/0290818 A1 | 9/2019 | Tuseth et al. |
| 2019/0314155 A1 | 10/2019 | Franklin et al. |
| 2019/0321049 A1 | 10/2019 | Herman et al. |
| 2019/0321172 A1 | 10/2019 | Gross et al. |
| 2019/0321531 A1* | 10/2019 | Cambronne ............ A61F 2/82 |
| 2019/0336285 A1 | 11/2019 | Quadri et al. |
| 2019/0350702 A1 | 11/2019 | Hernandez |
| 2019/0365535 A1 | 12/2019 | Sutherland et al. |
| 2019/0365538 A1* | 12/2019 | Chambers .......... A61F 2/2454 |
| 2019/0388218 A1 | 12/2019 | Vidlund et al. |
| 2019/0388222 A1 | 12/2019 | Drasler et al. |
| 2020/0000589 A1 | 1/2020 | Pasquino et al. |
| 2020/0008936 A1 | 1/2020 | Cheema et al. |
| 2020/0008940 A1 | 1/2020 | Nasr |
| 2020/0015965 A1 | 1/2020 | Lane et al. |
| 2020/0261219 A1* | 8/2020 | Kumar ............ A61B 17/12172 |

OTHER PUBLICATIONS

Notification of the International Preliminary Report on Patentability (Chapter I) for PCT/US2018/045030; dated Feb. 13, 2020.

International Preliminary Report on Patentability (Chapter I) for PCT/US2018/045030; dated Feb. 13, 2020.

* cited by examiner

100

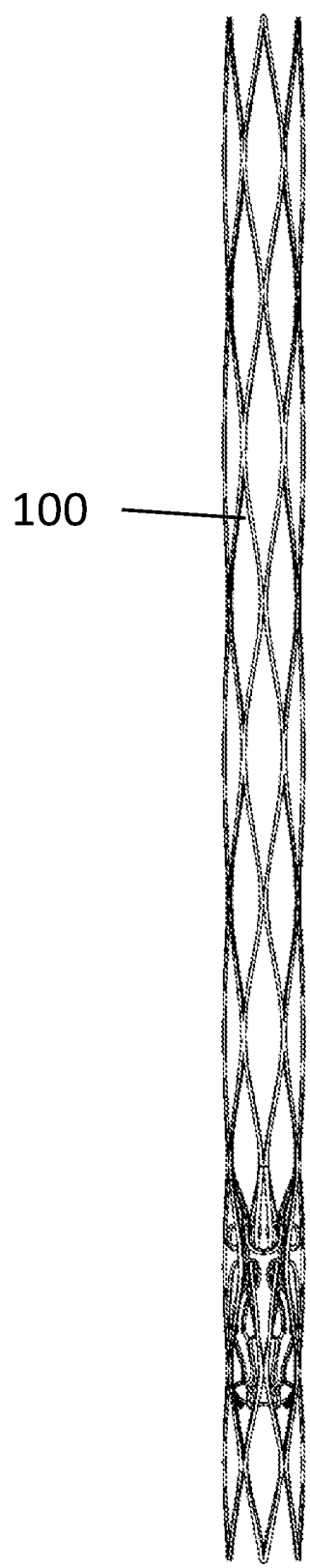
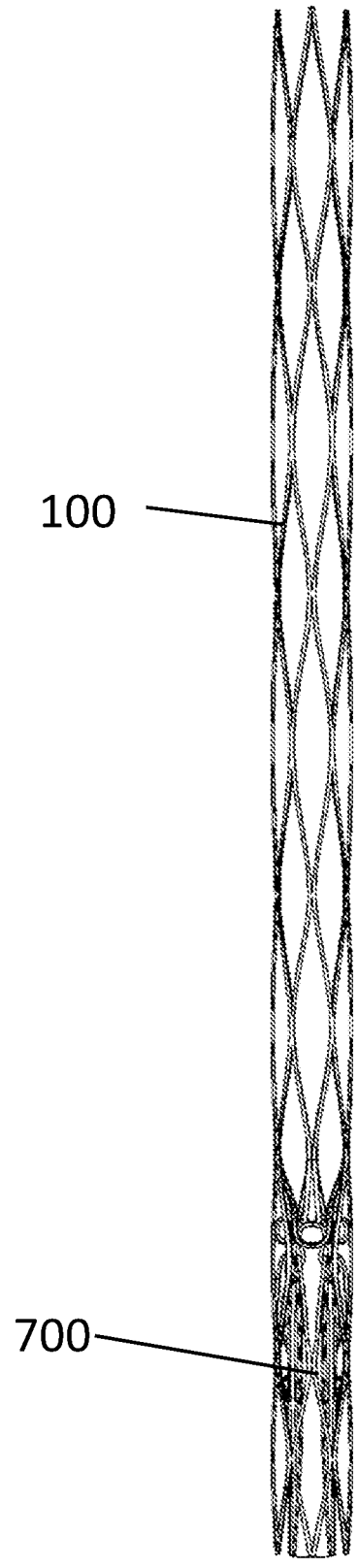
FIG. 18A
FIG. 18B

ATRIAL CAGE FOR PLACEMENT, SECURING AND ANCHORING OF ATRIOVENTRICULAR VALVES

CROSS-REFERENCE TO RELATED APPLICATIONS

This is a National Stage filing of PCT/US18/45030, filed on Aug. 2, 2018, which claims the benefit of priority of U.S. Provisional Application No. 62/540,916, filed Aug. 3, 2017, the entirety of which are incorporated herein by reference.

GOVERNMENT RIGHTS

This invention was made with Government support under Grant No. HL119893, awarded by the National Institutes of Health. The Government has certain rights in this invention.

BACKGROUND OF THE INVENTION

(1) Field of Invention

The present invention relates to heart valves and, more particularly, to a collapsible cage for percutaneous delivery and implantation of an atrioventricular valve within an atrium of the heart.

(2) Description of Related Art

Valvular heart disease is the third-most common cause of heart problems in the United States. While artificial valves have been developed to address such heart problems, such valves are often difficult to implant in a patient. Due to its minimally invasive nature, the percutaneous approach to aortic valve implantation has been a success, sparing patients aggressive surgery and reducing associated comorbidities. The lure of percutaneous technologies provides cost effective solutions to heart valve disease, thereby allowing more timely interventions with acceptable efficacy and minimal complications, especially for patients who cannot undergo surgery. Nevertheless, a problem with existing techniques is that they are difficult to securely anchor the transcatheter atrioventricular valve prosthesis at the atrioventricular junction (annulus).

Thus, a continuing need exists for a system for percutaneous delivery and implantation of an atrioventricular valve within an atrium of the heart that allows the transcatheter atrioventricular valve (AV) to be securely placed and anchored at the AV junction.

SUMMARY OF INVENTION

The present invention relates to heart valves and, more particularly, to a collapsible atrial cage for percutaneous delivery and implantation of an atrioventricular valve within an atrium of the heart. The atrial cage includes an atrial portion and a ventricular portion attached with and separated from the atrial portion by a valve juncture portion.

In other aspects, the atrial cage includes at least one interlock shaped to lock with and secure an atrioventricular valve proximate the valve juncture portion. Additionally, each interlock includes a tip clasp and a base clasp, whereby the tip clasp is shaped to lock with a valve catch tip and the base clasp is shaped to at least partially wrap around a valve catch base.

In another aspect, the atrial cage is collapsible and expandable, such that when expanded, each of the atrial portion, ventricular portion and valve juncture portion have a diameter such that the diameter of the atrial portion and ventricular portion is greater than the diameter of the valve juncture portion.

In yet another aspect, the atrial cage is a wire cage.

In another aspect, the atrial cage is wire cage formed of Nitinol wire.

Further and in yet another aspect, the atrial cage is self-expandable.

Additionally and in another aspect, the atrial cage is balloon-expandable.

In another aspect, an atrioventricular valve is secured proximate the constricted portion of the atrial cage, whereby the cage is securely attached to the atrioventricular valve before delivery to an atrium using a transcatheter delivery system.

In another aspect, the atrial cage is formed in whole or part of a dissolving material, whereby the atrial cage may gradually resorb or dissolve away after some time period and after an atrioventricular valve becomes secured to an atrioventricular juncture.

Additionally, the atrial cage is sized and shaped according to medical imaging to fit or conform with atrial anatomy of a subject.

Further the atrial cage is sized and shaped such that once deployed and expanded, at least a part of the cage is in contact with the atrial wall.

In another aspect, the atrial cage is sized and shaped based on three-dimensional scanning of a subject to fit the subject's anatomy.

In yet another aspect, the atrial cage is laser-cut from a tube

Additionally, the atrial cage is formed through three-dimensional printing.

In yet another aspect, the atrial cage is collapsible over a catheter for percutaneous delivery and deployable alone for subsequent delivery and attachment of a valve.

In another aspect, the atrial cage includes a valve collapsed therein and is collapsible over a catheter for percutaneous delivery and deployment simultaneously with the valve.

In other aspects and as can be appreciated by one skilled in the art, the present invention also comprises a method for using the atrial cage as described herein. For example, this disclosure provides a method for percutaneously delivering and implantation of an atrial cage, comprising acts of: delivering an atrial cage with a delivery system to a desired location inside a subject's heart chamber, such that during delivery, the atrial cage is collapsed within a sheath of the delivery system; retracting the sheath to deploy the atrial cage at the desired location, such that upon deployment the atrial cage expands at the desired location; delivering a valve with a delivery system to a desired location within the deployed atrial cage; and releasing and implanting the heart valve at the desired location within the deployed atrial cage.

In another aspect, the method for percutaneously delivering and implantation of an atrial cage having a valve therein comprises acts of: delivering an atrial cage having valve therein with a delivery system to a desired location inside a subject's heart chamber, such that during delivery, both the atrial cage and valve are collapsed within a sheath of the delivery system; retracting the sheath to deploy the atrial cage at the desired location, such that upon deployment, both the atrial cage and valve expand at the desired location; and releasing and implanting the atrial cage with attached heart valve at the desired location.

Finally, as can be appreciated by one in the art, the present invention also comprises a method for forming atrial cage and components as described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 18A is a side-view illustration depicting the atrial cage in a collapsed configuration without a valve prosthesis therein;

FIG. 18B is a side-view illustration depicting the atrial cage in the collapsed configuration with a valve prosthesis positioned therein in the collapsed form;

DETAILED DESCRIPTION

The present invention relates to heart valves and, more particularly, to a collapsible cage for percutaneous delivery and implantation of an atrioventricular valve within an atrium of the heart. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35

U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object. Further details are provided below.

(1) Specific Details

Figure 7A:
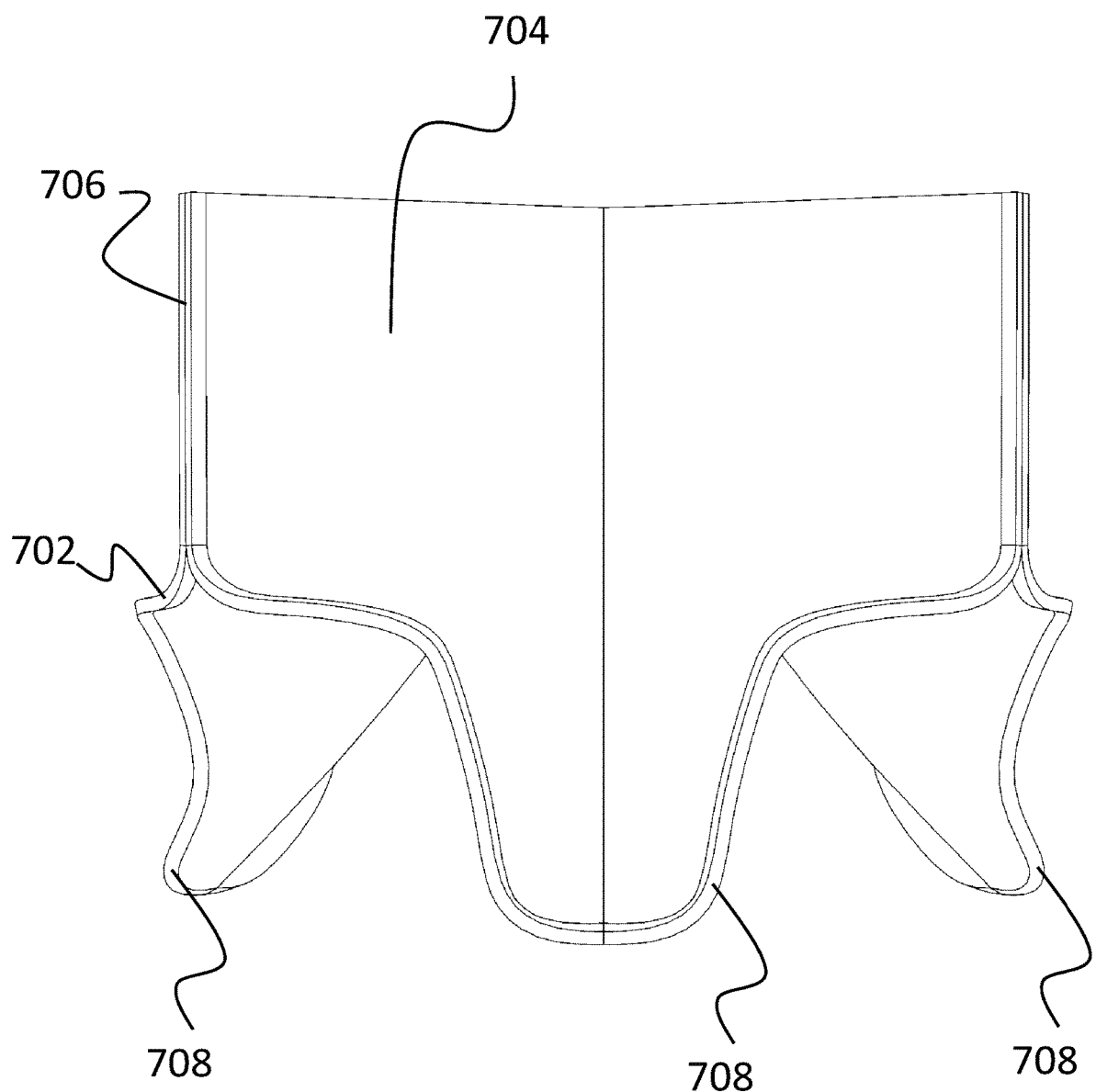
FIG. 7A is a front-view illustration of an example valve as can be delivered using the atrial cage according to various embodiments of the present invention.
Figure 7B:
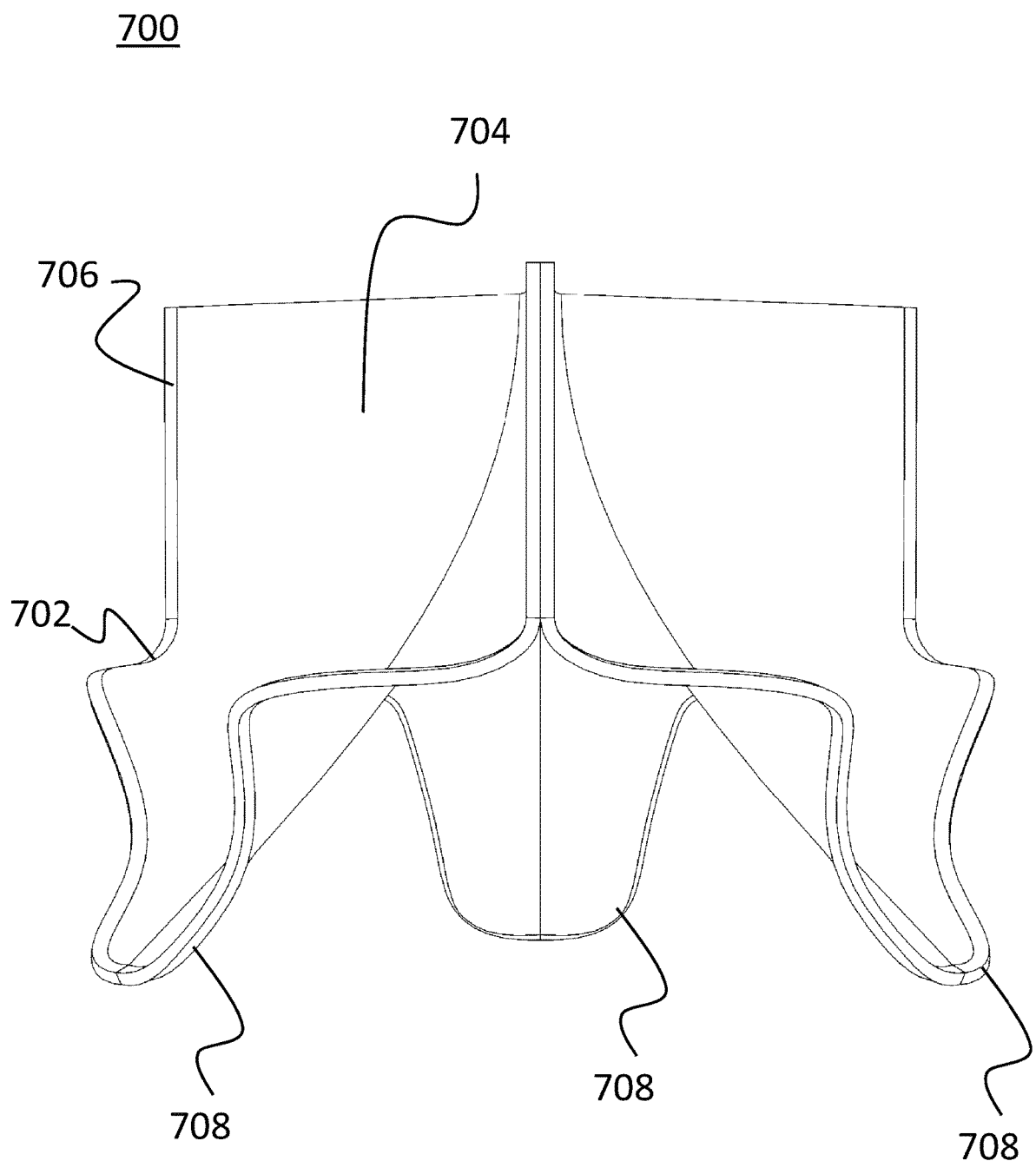
FIG. 7B is a rear-view illustration of the example valve as illustrated in FIG. 7A.
Figure 7C:
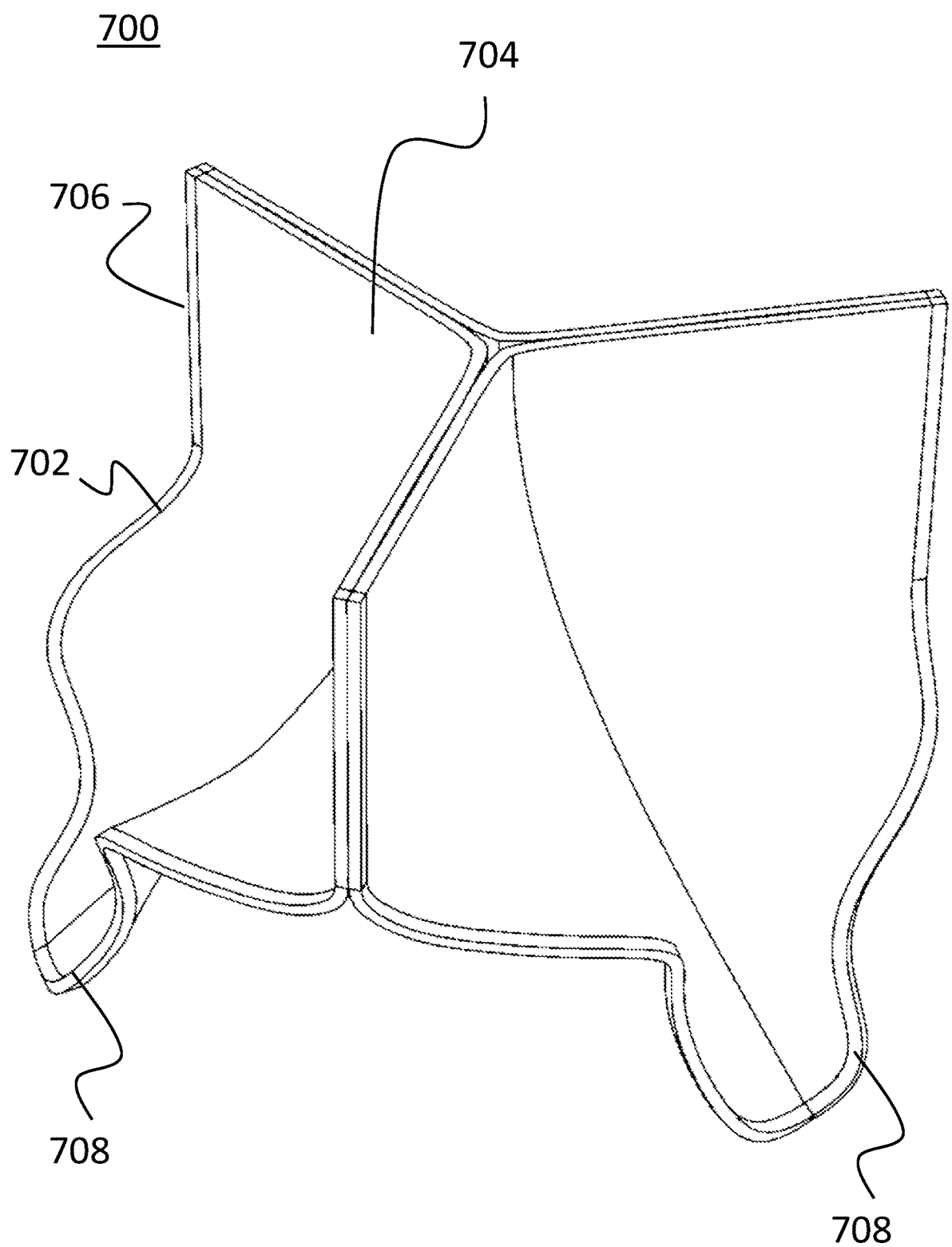
FIG. 7C is an isometric-view illustration of the example valve as illustrated in FIG. 7A.

As shown in FIGS. 1 through 15, this disclosure is directed to a collapsible (and expandable) atrial cage 100. The atrial cage 100 is designed for percutaneous delivery and implantation of atrioventricular valves within an atrium of the heart. The atrial cage 100 provides a means for a transcatheter atrioventricular (AV) valve (examples of which are depicted in FIGS. 7A through 7C) to be securely placed and anchored at the AV junction (as shown between FIGS. 16A and 16B). FIG. 16A depicts an interior-view illustration of a heart chamber, depicting a native mitral valve annulus 1600, while FIG. 16B depicts the atrial cage 100 and a bioprosthetic mitral valve 700 securely anchored at the AV junction. Further details regarding the atrial cage 100 and a corresponding valve 700 are provided below.

The collapsible atrial cage 100 is sized and shaped to fit a patient atrium. The cage is securely attached or securely attachable to a transcatheter AV valve prosthesis. Once deployed and expanded in the atrium, the cage 100 is strong enough to securely anchor the AV valve prosthesis in place (i.e., at an atrioventricular junction such as mitral and/or tricuspid valve's annulus). Through use of the wireform (on various embodiments) and its shape, the atrial cage 100 is structured so as to not interfere with atrial function.

Figure 1:
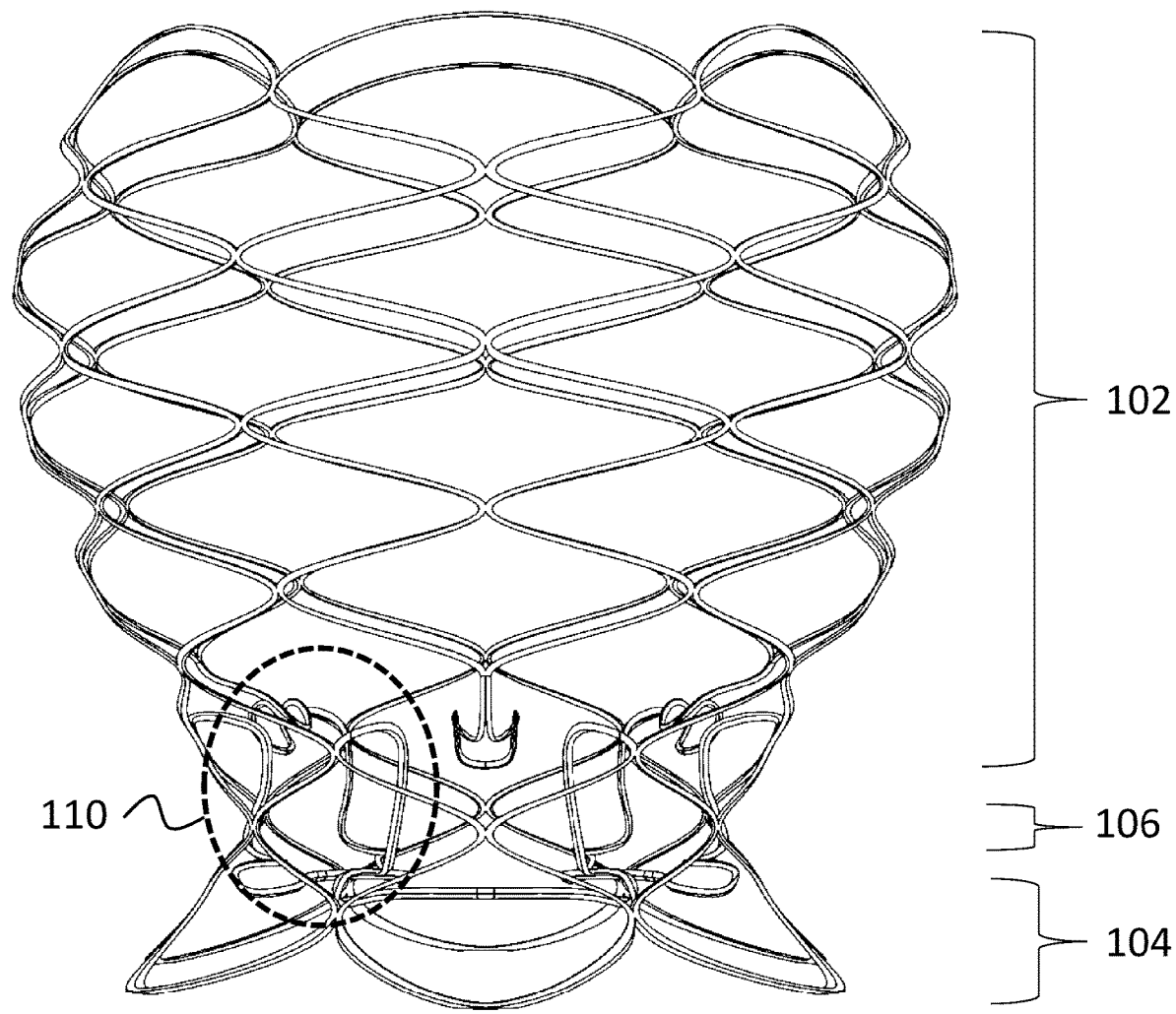
FIG. 1 is a front-view illustration of an atrial cage according to various embodiments of the present invention.
Figure 2:
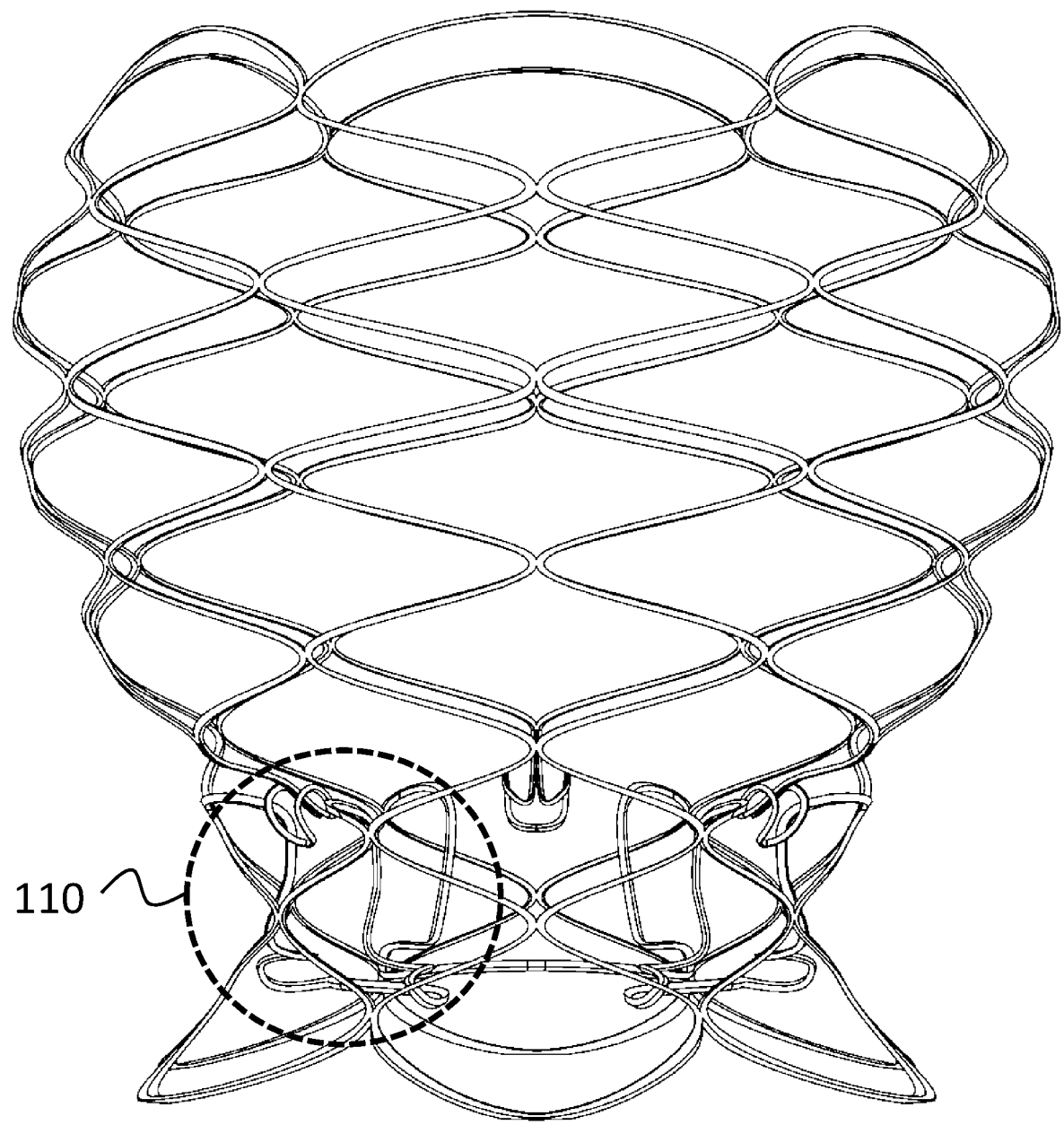
FIG. 2 is a rear-view illustration of the atrial cage according to various embodiments of the present invention.
Figure 3:
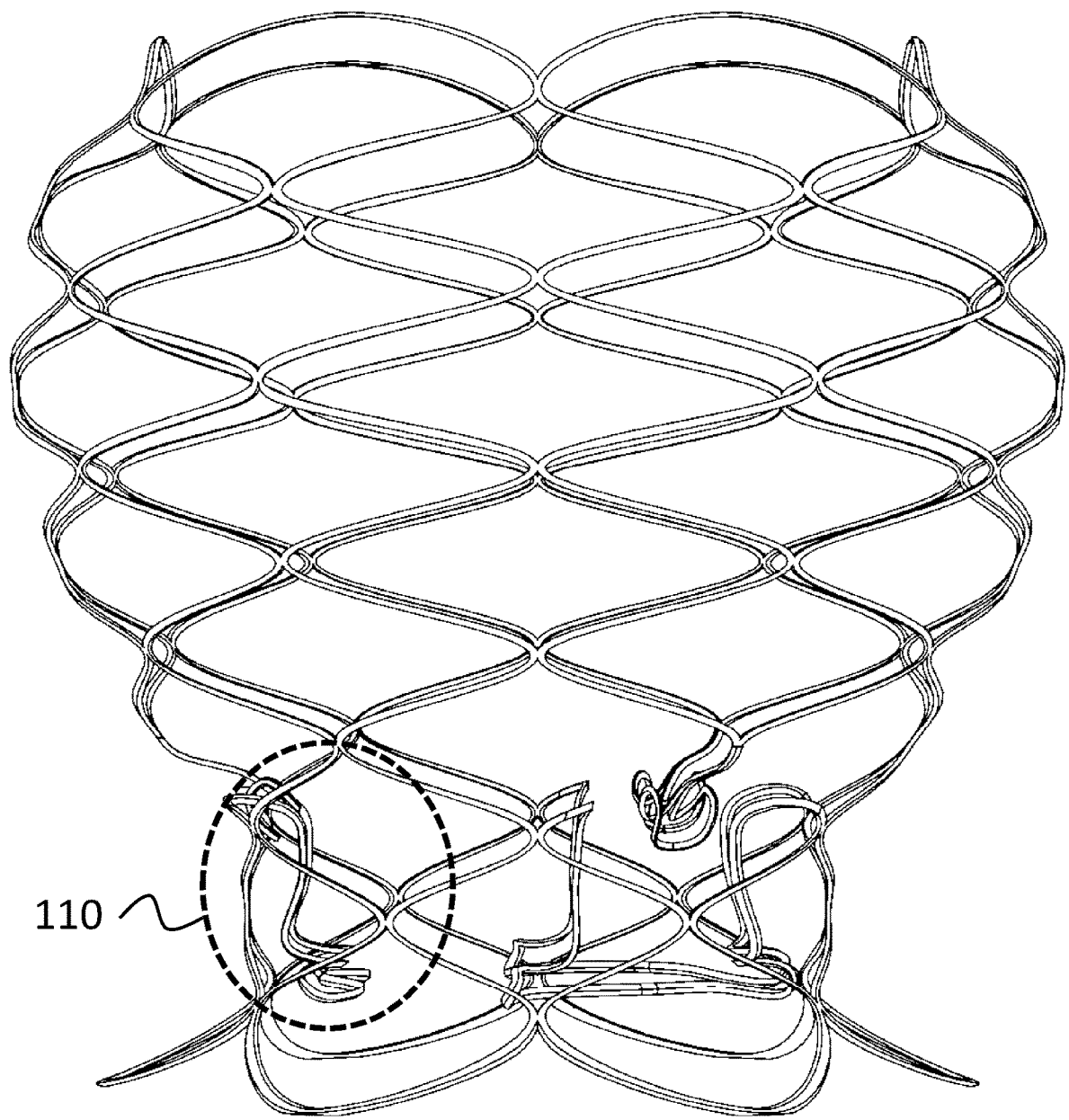
FIG. 3 is a left-view illustration of the atrial cage according to various embodiments of the present invention.
Figure 4:
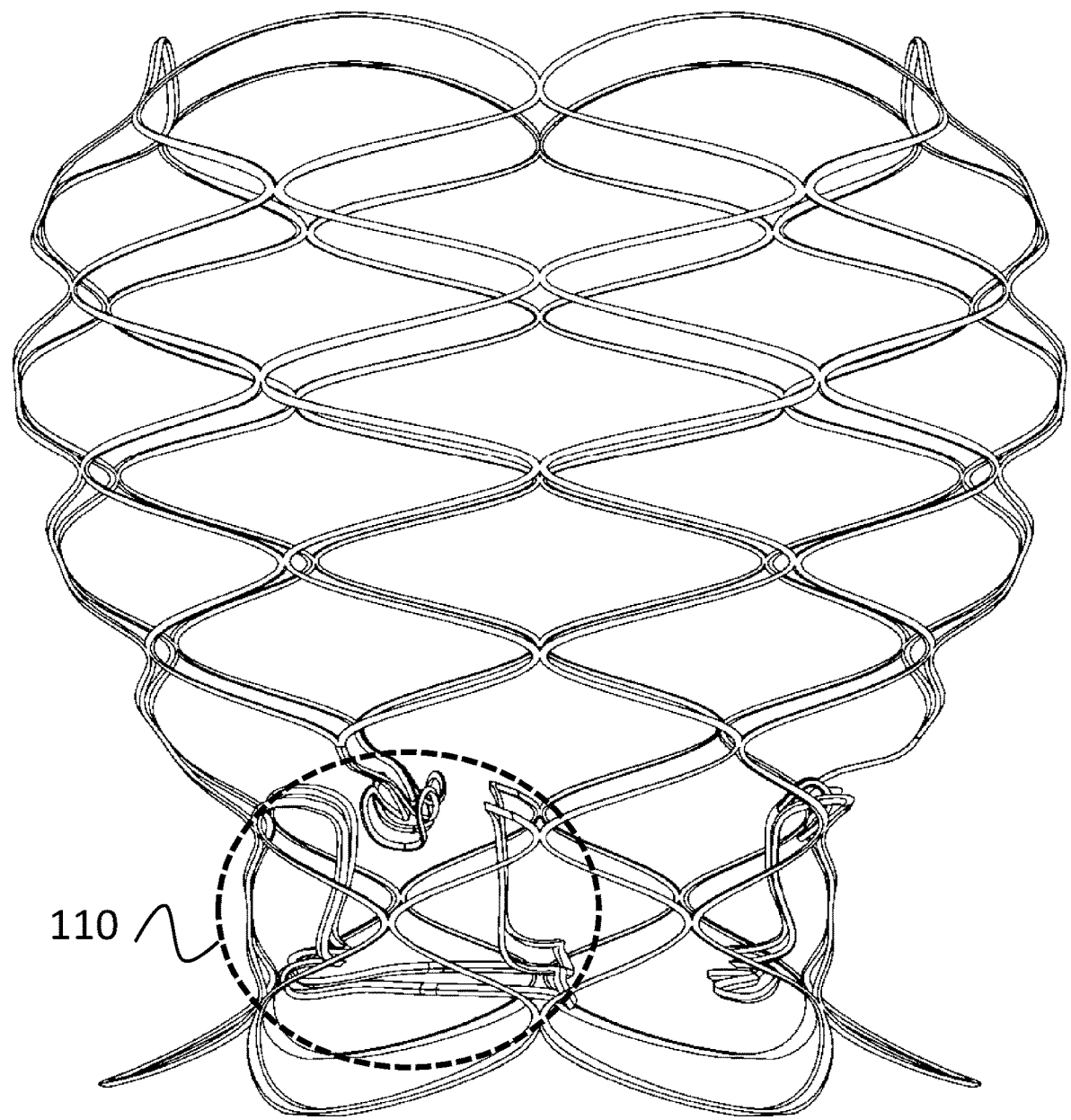
FIG. 4 is a right-view illustration of the atrial cage according to various embodiments of the present invention.
Figure 5:
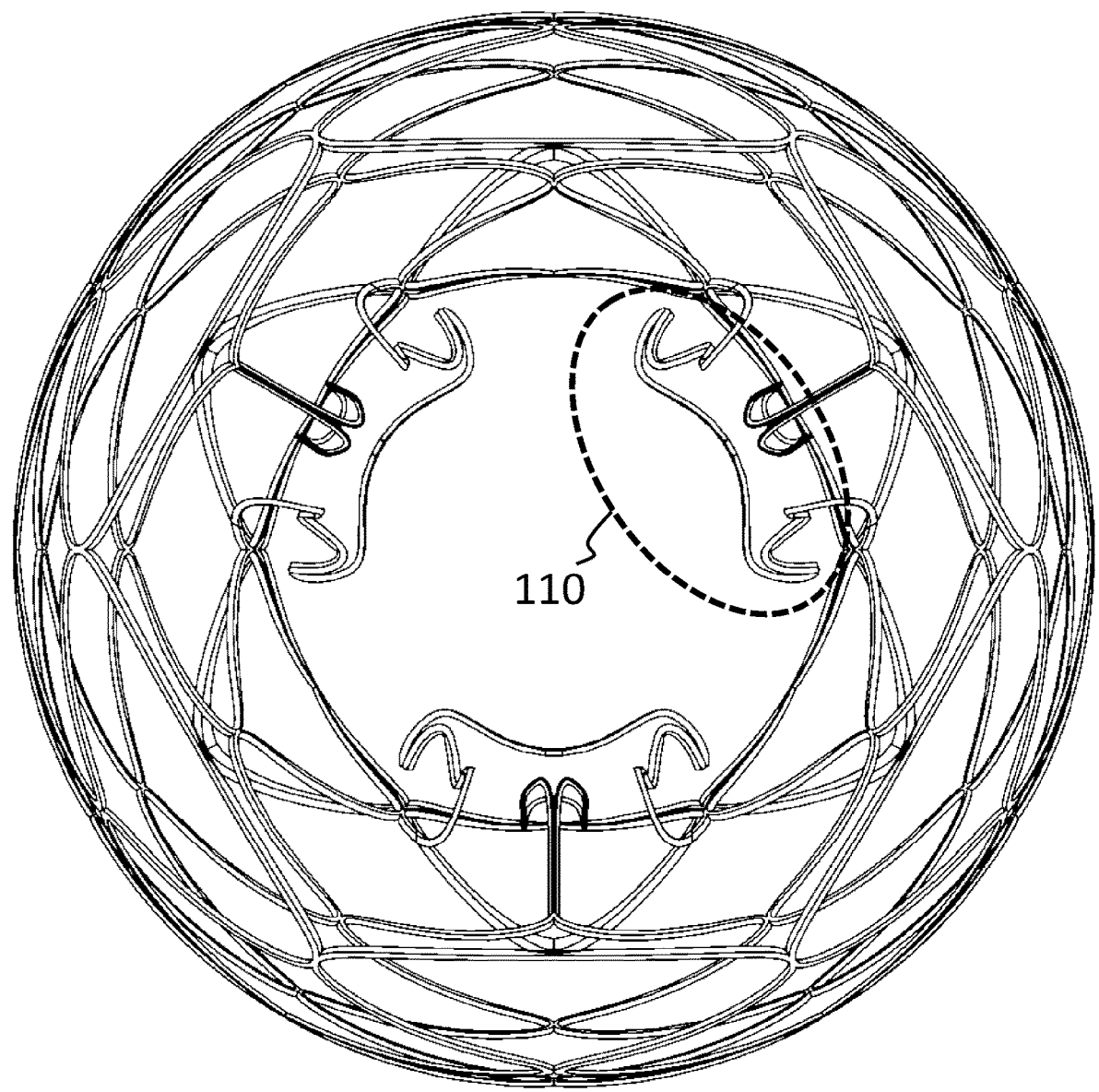
FIG. 5 is a top-view illustration of the atrial cage according to various embodiments of the present invention.
Figure 6:
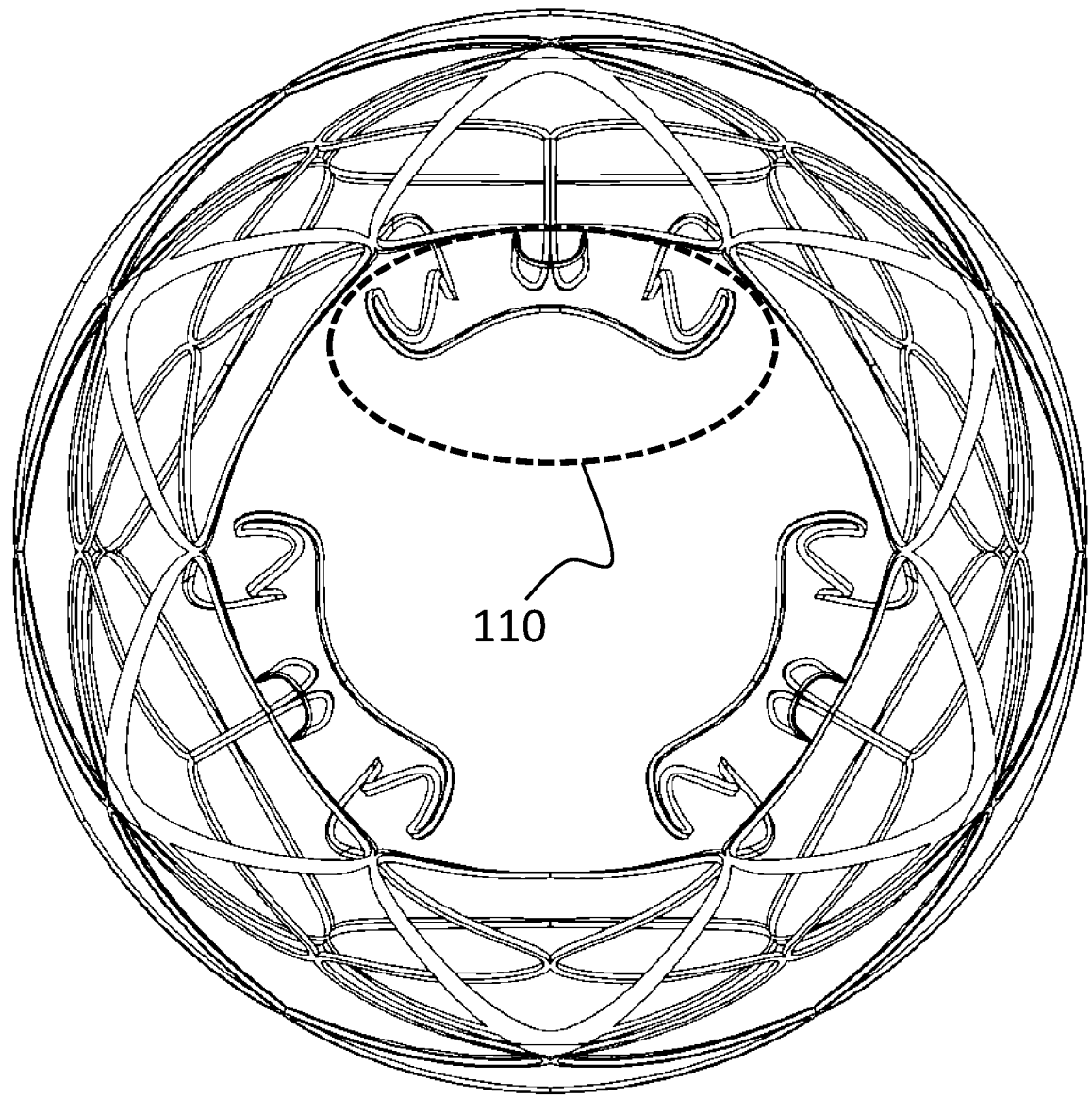
FIG. 6 is a bottom-view illustration of the atrial cage according to various embodiments of the present invention.

In various embodiments and as shown in FIG. 1, the atrial cage 100 is a wire cage (although not limited thereto) that is formed and shaped to include an atrial portion 102 (also referred to as an atrial component) and a ventricular portion 104 (also referred to as a ventricular component). The atrial portion 102 and ventricular portion 104 are separated by a valve juncture portion 106 (also referred to as a valve juncture component). The ventricular portion 104 operates as an extension into the native ventricle through which the AV junction encircles the cage 100 structure. Notably and when expanded as shown in the figures, the atrial portion 102 and ventricular portion 104 each have a diameter that is greater than the diameter of the valve juncture portion 106. The larger diameters of the atrium and ventricular portions 102 and 104 allow the atrial cage 100 to securely attach on opposing sides of the AV juncture (with the valve juncture portion 106 positioned within the AV juncture) to anchor the AV valve prosthesis to the AV juncture while avoiding unnecessary contact with select areas of the atrial wall. Thus, due to the larger diameters of the atrium and ventricular portions 102 and 104, the atrial cage 100 is securely connected to and holds an AV valve in place and, notably prevents the AV valve and atrial cage 100 from sliding into the atrium or ventricle. For further understanding, FIG. 2 through 6 provide rear, left, right, top, and bottom views, respectively, of the atrial cage 100.

As noted above, the atrial cage 100 is formed to securely hold a prosthetic AV valve at the AV junction. In various embodiments, the AV valve is integrally formed as a part of the atrial cage 100. However and in other embodiments, the AV valve is separate part attached to the atrial cage 100 using any suitable connection device or technique, non-limiting examples of which include suture, mechanical interlock, and material fusion. For example and regarding the mechanical interlock, the atrial cage 100 can be formed with one or more cage interlocks that are shaped to interlock with a corresponding valve catch. While the cage interlocks 110 are depicted throughout FIGS. 1 through 6, they are more clearly seen in the top and bottom views provided in FIGS. 5 and 6, respectively. The non-limiting example as depicted illustrates a set of three cage interlocks 110 on the cage 100. Although not depicted, the catch or other parts of the valve can be alternatively sutured or otherwise material fused to the cage 100 at the appropriate location.

However and as noted above, the cage interlocks 110 are specifically shaped to interlock with and securely hold an AV valve. A non-limiting example of such a suitable AV valve 700 is depicted in FIGS. 7A through 7C and described in U.S. patent application Ser. No. 15/598,210, filed on May 17, 2017, entitled, "Collapsible Atrioventricular Valve Prosthesis" and published as U.S. Patent Publication No. 2017-0252163, the entirety of which are hereby incorporated herein by reference. The AV valve 700 includes a frame 702 and a plurality of leaflets 704 separated by upstanding prongs 706. In this non-limiting example, between each prong 706 there is at least one catch 708 formed on the frame 702 that protrudes downward from the frame 702 (when the prongs 706 project upward). The catch 708 is an appendix or fixture that is shaped (e.g., includes a hook-shaped or curvature) to act as a catch or clamp to hold the valve frame 702 secure on the atrioventricular junction or at the atrial side of the heart when installed and deployed. Alternatively, when used with an atrial cage, the catch 708 can be securely held by the cage interlocks 110 which grasp and securely hold the catch 708 and corresponding valve 700.

Figure 8A:
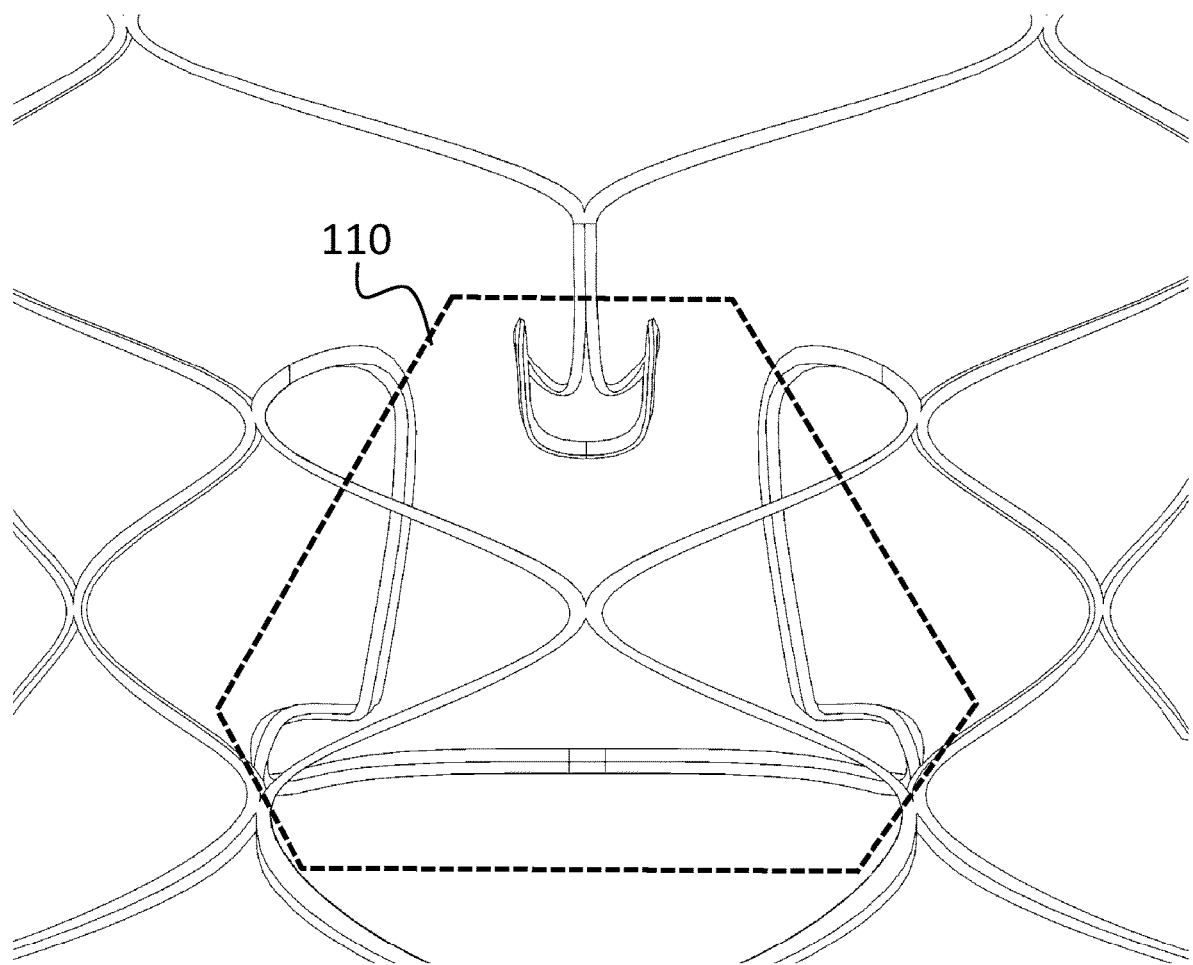
FIG. 8A is a front, close-up view illustration of an interlock as formed on the atrial cage according to various embodiments of the present invention.
Figure 8B:
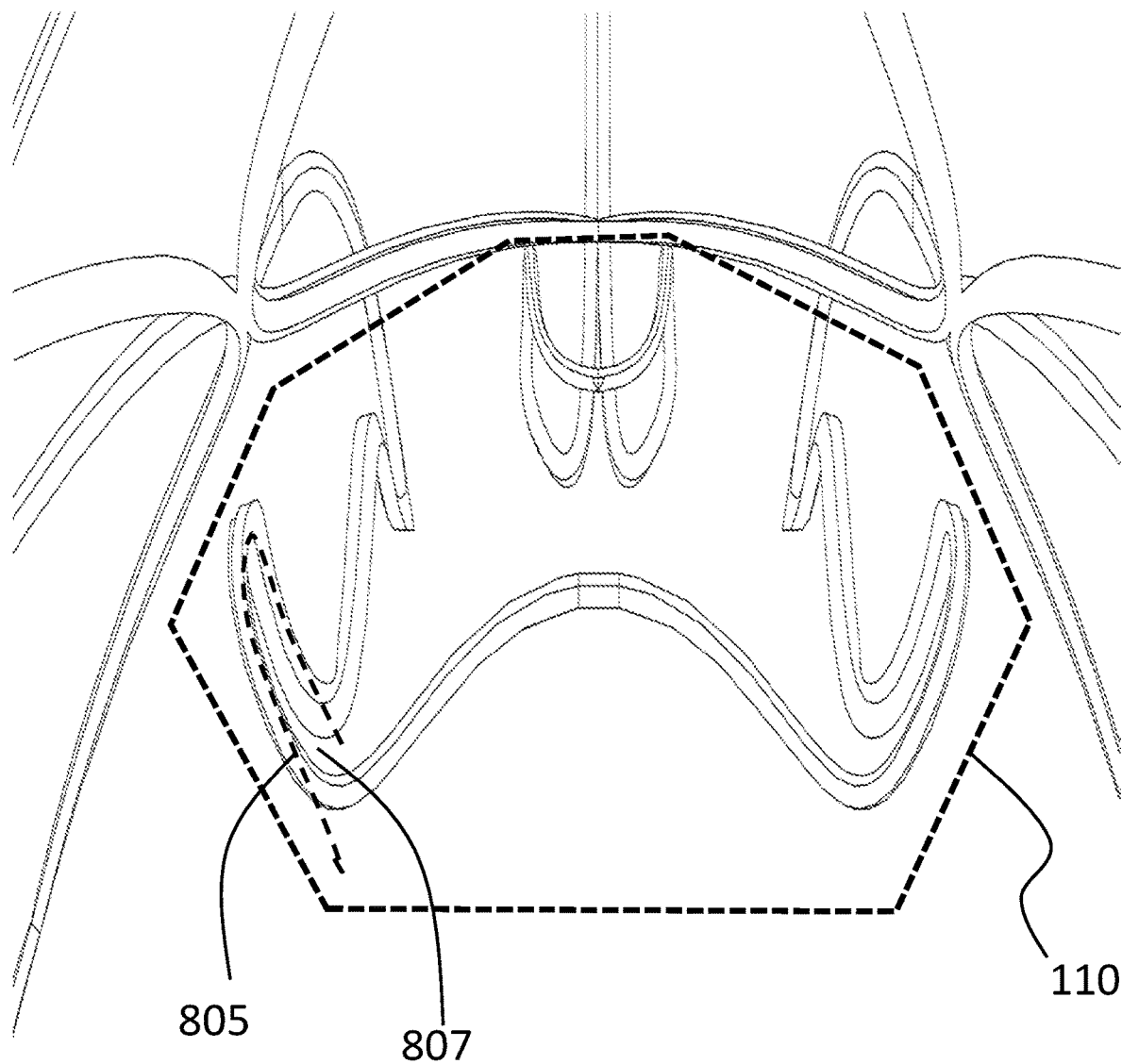
FIG. 8B is a bottom, close-up view illustration of the interlock according to various embodiments of the present invention.
Figure 8C:
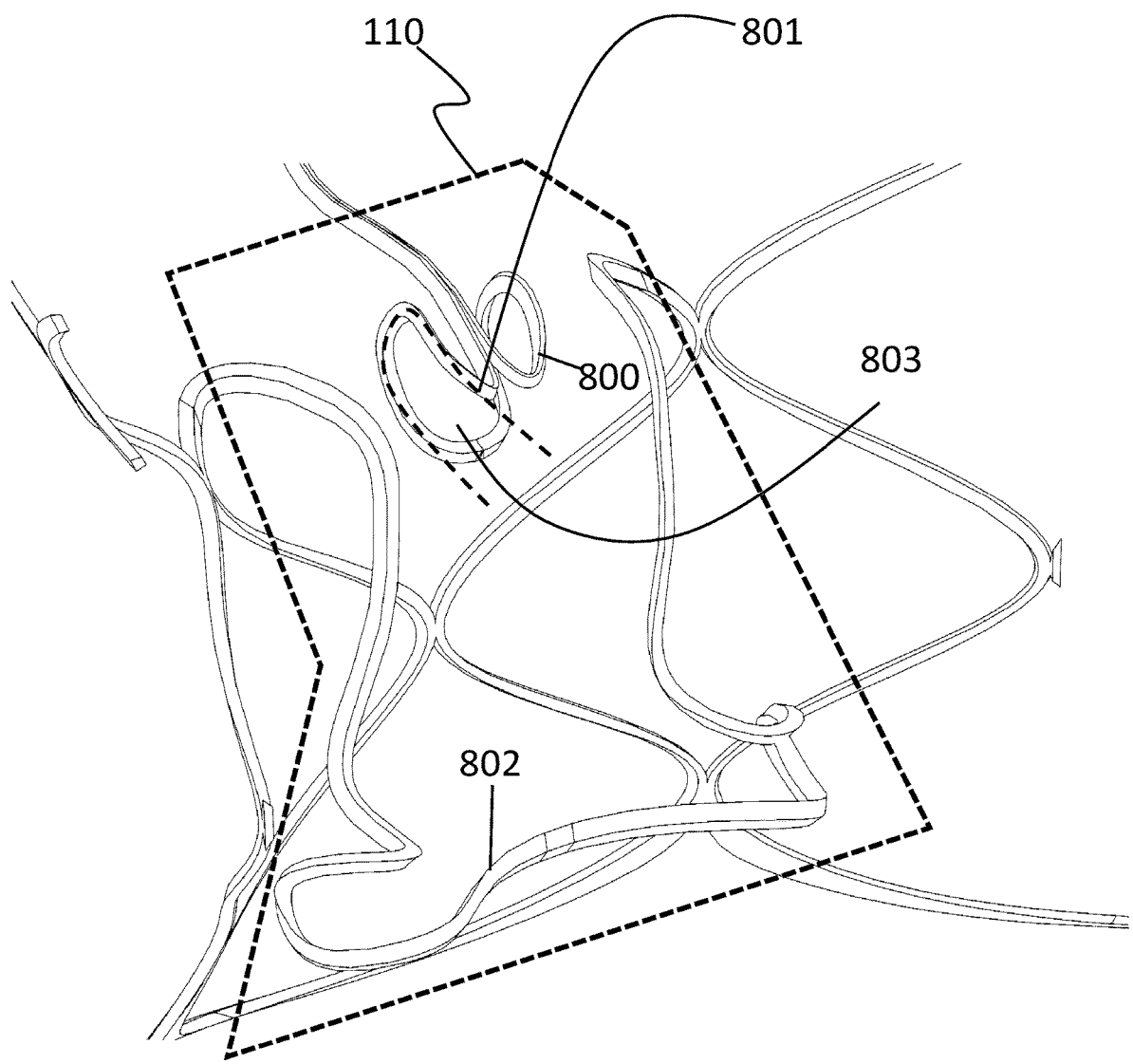
FIG. 8C is an isometric, close-up view illustration of the interlock according to various embodiments of the present invention.
Figure 17:
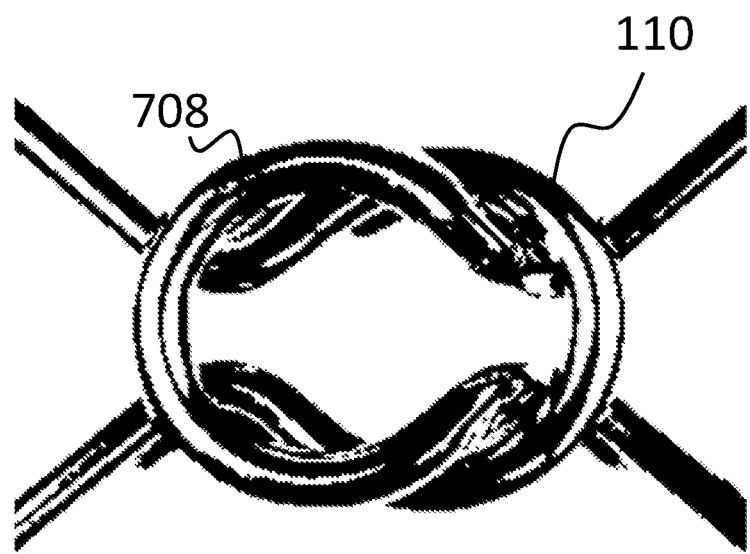
FIG. 17 is an illustration depicting an example of a locking configuration of an interlock and catch according to various embodiments of the present invention.

For further understanding, FIGS. 8A through 8C provide front, bottom, and isometric, close-up view illustrations of the cage interlock 110. FIGS. 8A through 8C are to be contrasted with FIGS. 9A through 9C, which depict a valve 700 and its catch 708 as secured with the interlocks 110 illustrated in FIGS. 8A through 8C. As can be appreciated by those skilled in the art, there are a number of interlock 110 shapes that can be employed to interlock with the catch 708. For example and as depicted in FIG. 17, the interlock 110 can be formed as a simple loop shape through which the catch 708 is formed and shaped to slip through and engagingly lock with the loop shape of the interlock 110.

Figure 9A:
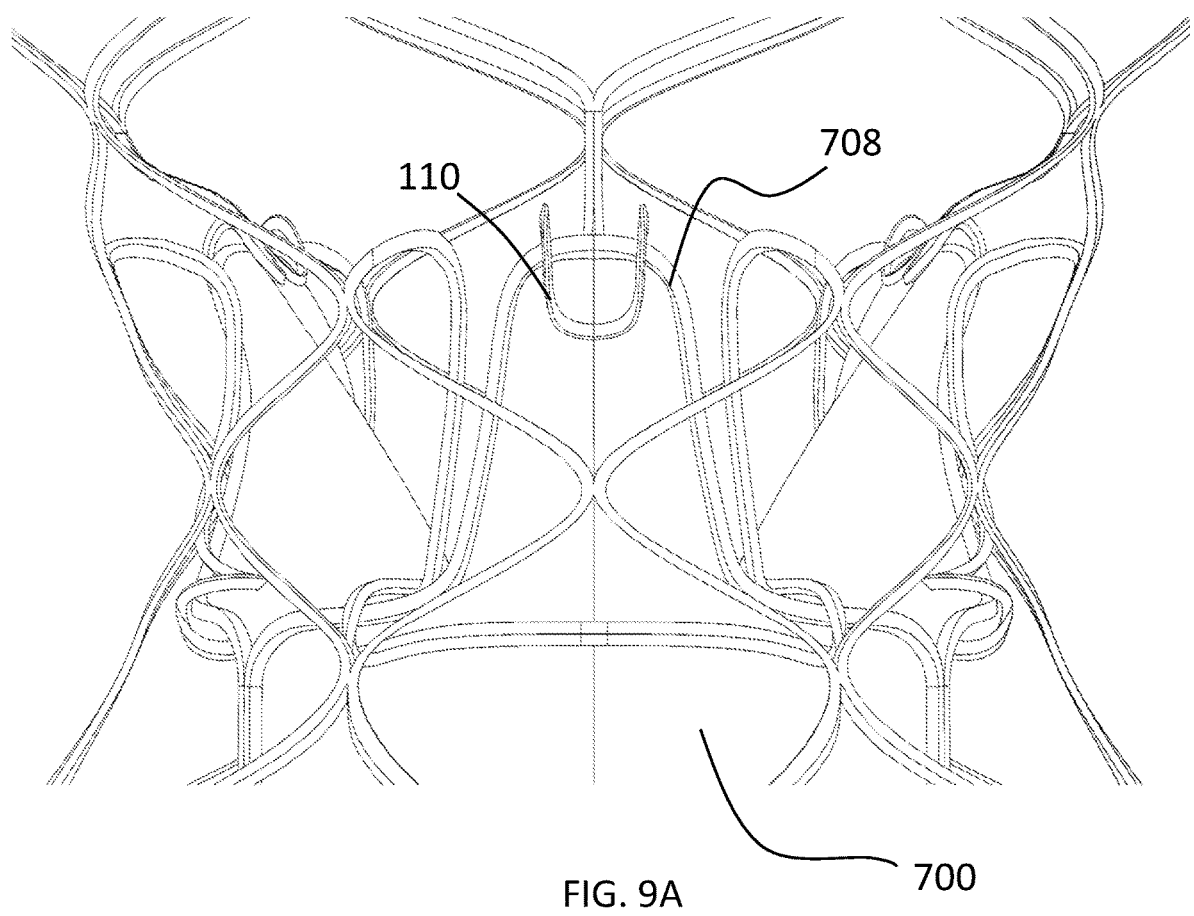
FIG. 9A is a front, close-up view illustration of the interlock, depicting the interlock as connected with a valve according to various embodiments of the present invention.
Figure 9B:
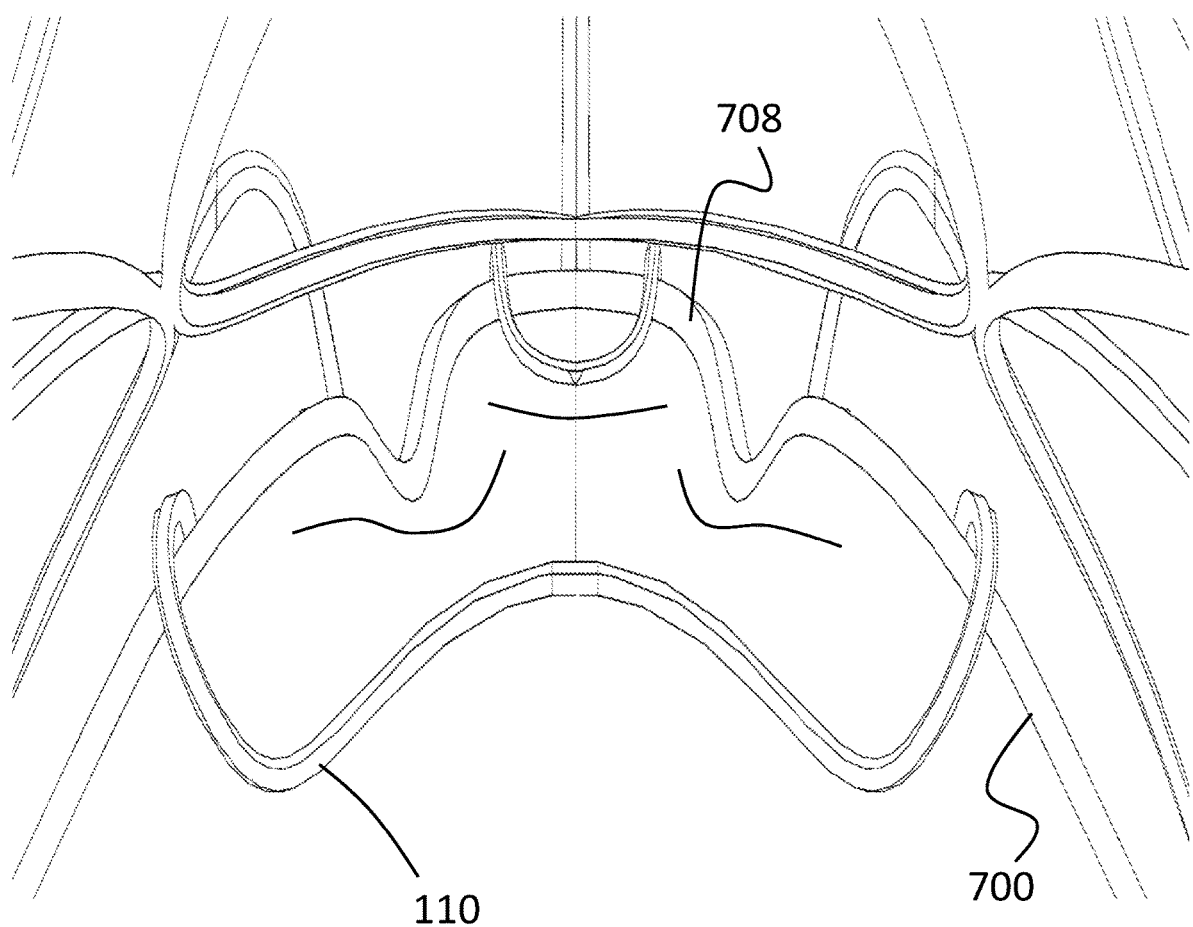
FIG. 9B is a bottom, close-up view illustration of the interlock connected with the valve according to various embodiments of the present invention.
Figure 9C:
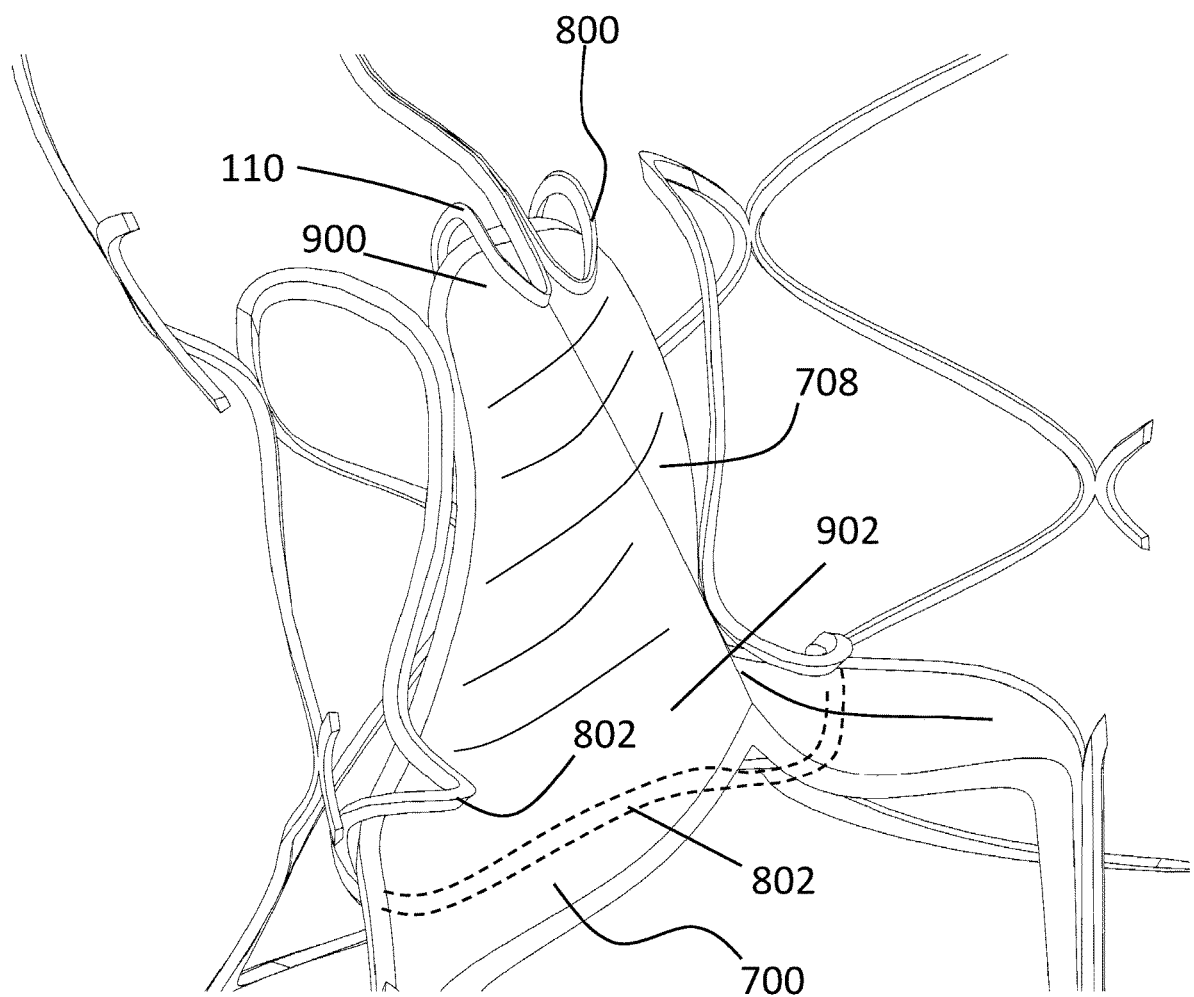
FIG. 9C is an isometric, close-up view illustration of the interlock connected with the valve according to various embodiments of the present invention.
Figure 10:
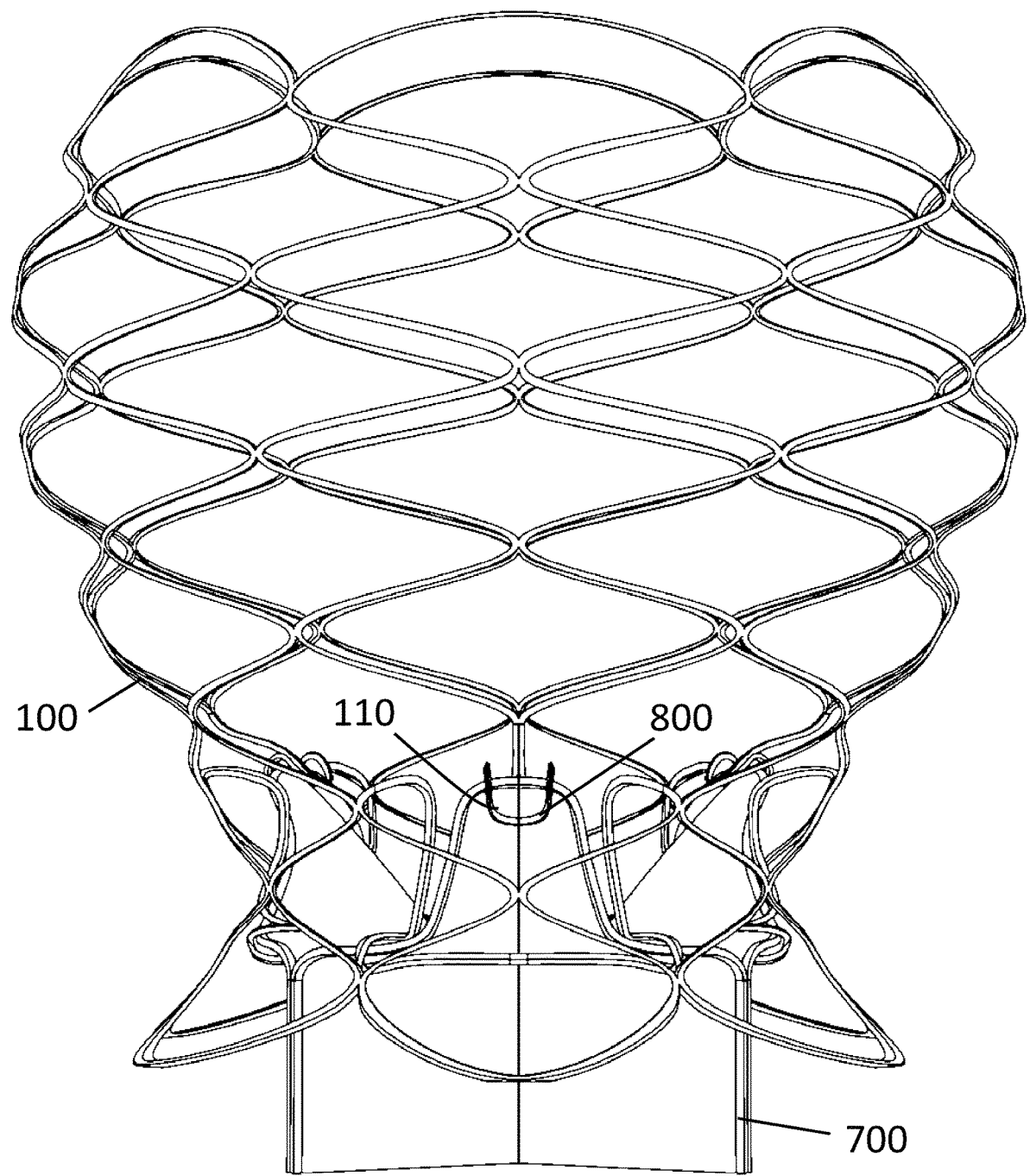
FIG. 10 is a front-view illustration of the atrial cage, depicting the atrial cage and corresponding interlock as connected with a valve according to various embodiments of the present invention.
Figure 11:
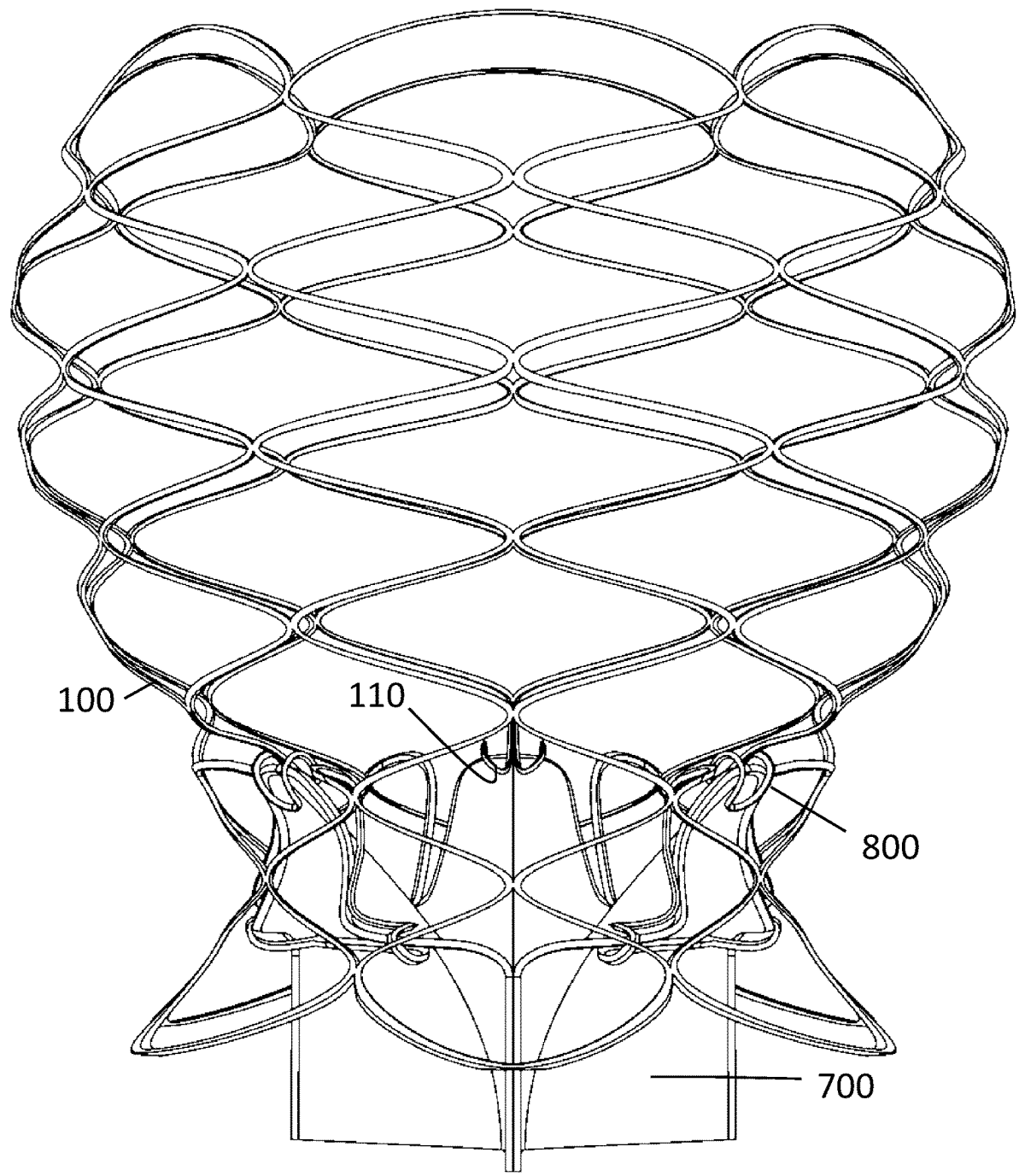
FIG. 11 is a rear-view illustration of the atrial cage, depicting the atrial cage and corresponding interlock as connected with a valve according to various embodiments of the present invention.
Figure 12:
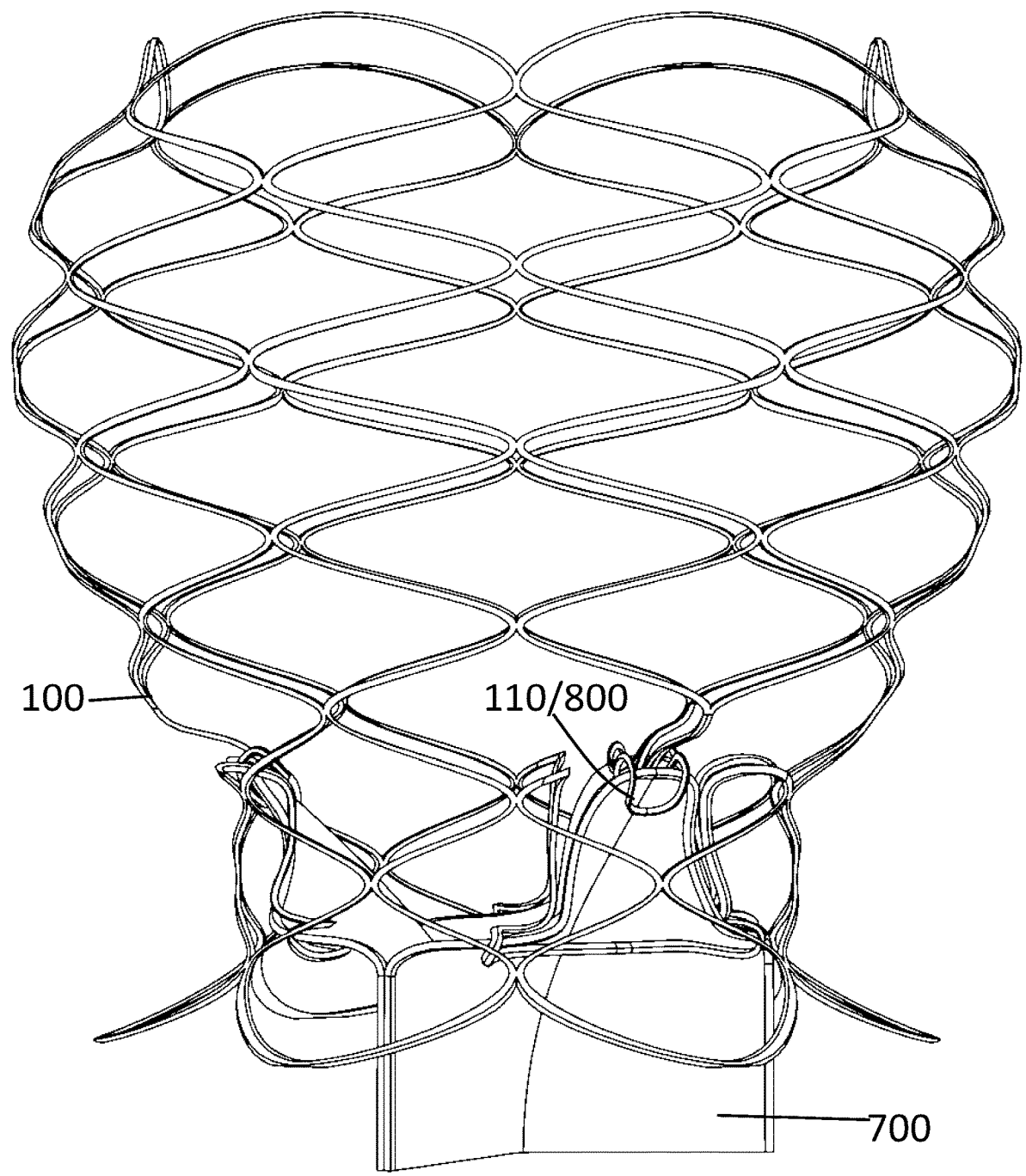
FIG. 12 is a left-view illustration of the atrial cage, depicting the atrial cage and corresponding interlock as connected with a valve according to various embodiments of the present invention.
Figure 13:
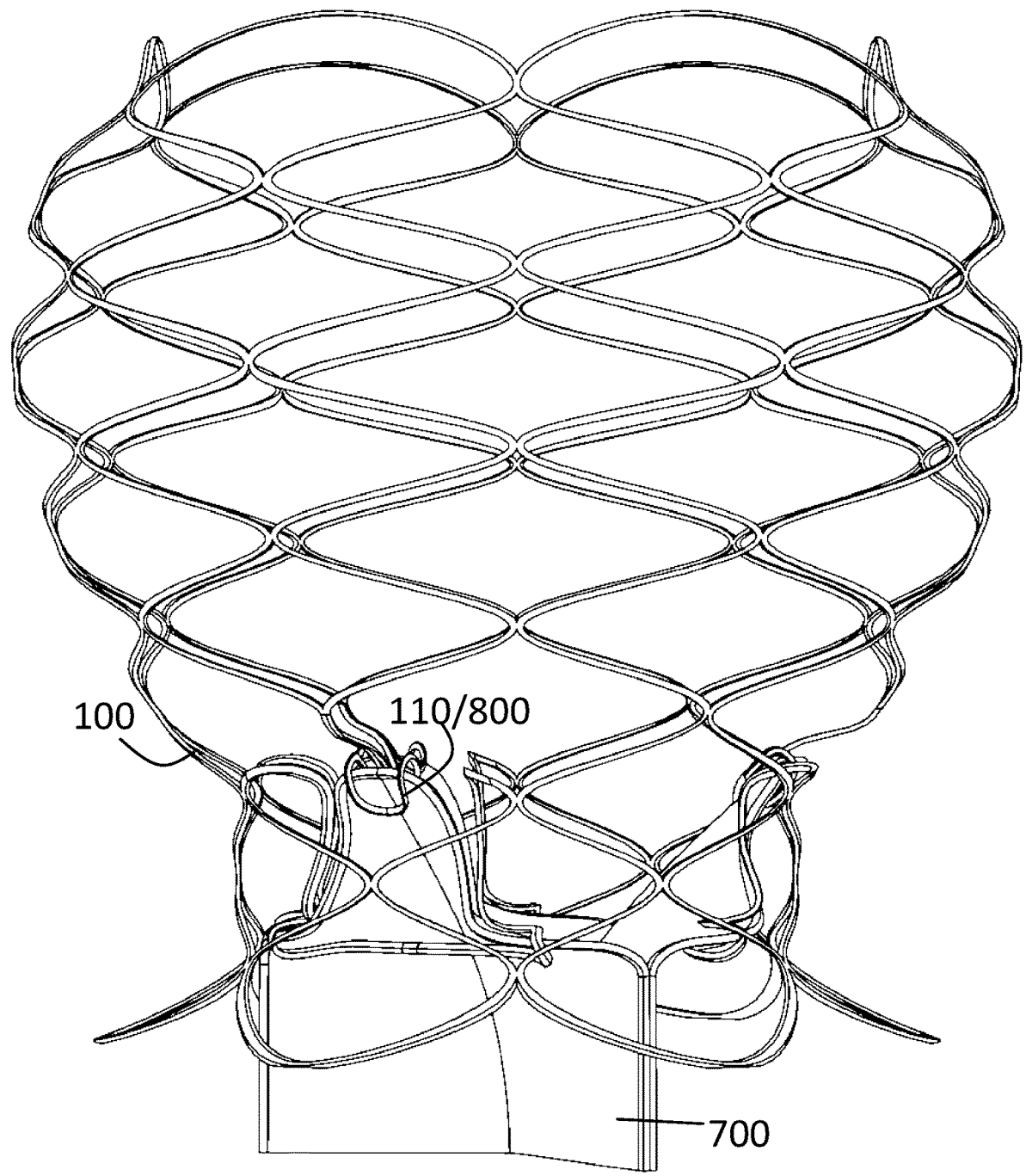
FIG. 13 is a right-view illustration of the atrial cage, depicting the atrial cage and corresponding interlock as connected with a valve according to various embodiments of the present invention.
Figure 14:
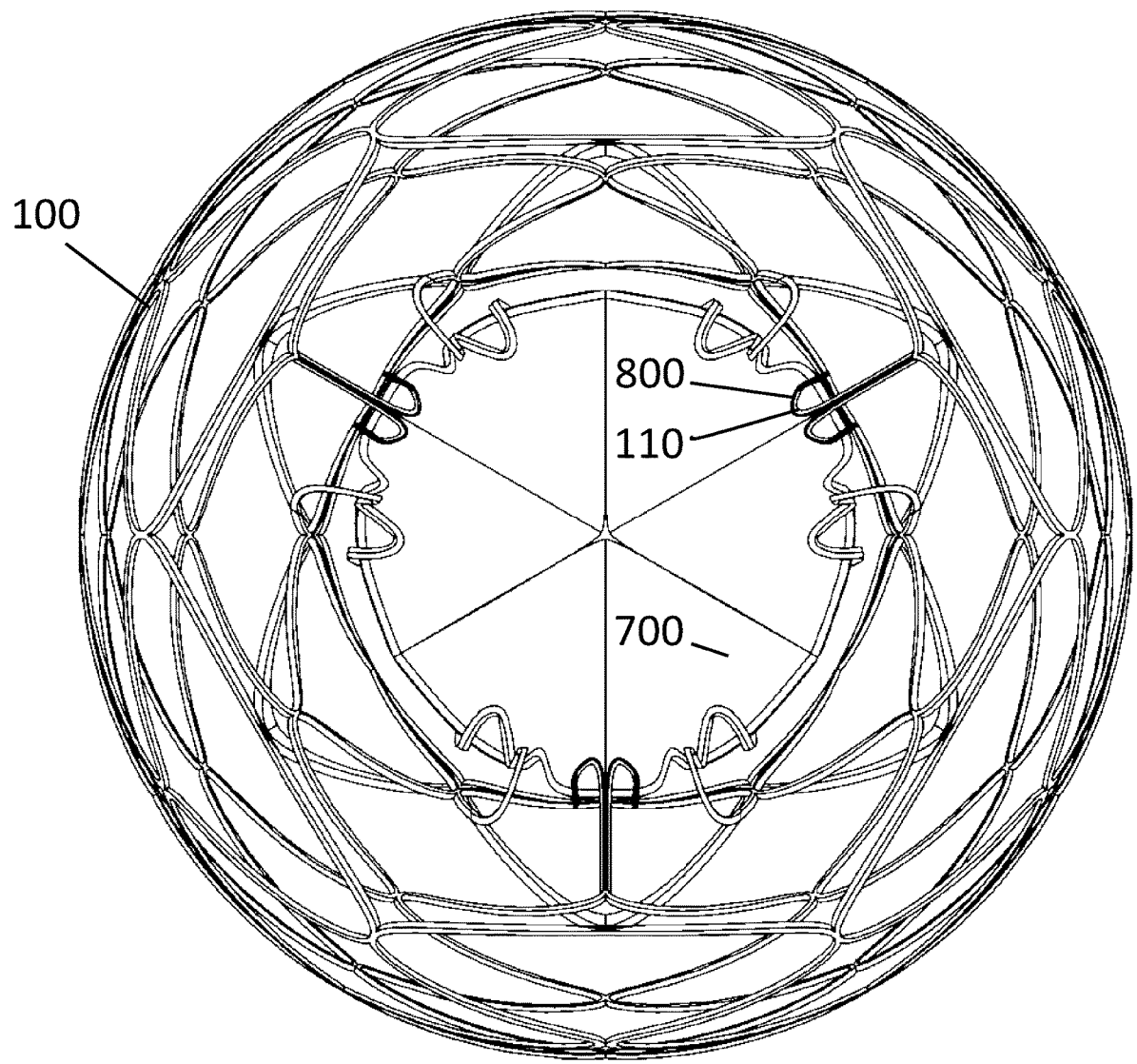
FIG. 14 is a top-view illustration of the atrial cage, depicting the atrial cage and corresponding interlock as connected with a valve according to various embodiments of the present invention.

Another non-limiting example is depicted throughout the figures and clearly shown in FIG. 8C. In this non-limiting example, the interlock 110 includes a tip clasp 800 (i.e., a first wireform locking mechanism that is a first three-dimensionally spatially curved clasp 801 having a folded U-shape with a first open end 803) and a base clasp 802 (i.e., as shown in FIG. 8B, a second wireform locking mechanism that is also a second three-dimensionally spatially curved clasp 805 having a second folded U-shape with a second open end 807). The tip clasp 800 is formed to engagingly receive and securely hold the tip of the catch while the base clasp 802 is formed to at least partially wrap around the base of the catch. This aspect is shown in FIG. 9C, which depicts a tip 900 of the catch 708 as nested into the tip clasp 800 while the base clasp 802 partially wraps around the base 902 of the catch 708. The base clasp 802 operates as a locking hoop similar to the aspect as depicted in FIG. 17; however, the added tip clasp 800 further secures the catch 708 to prevent or otherwise minimize any rocking, slipping, or unwanted motion of the valve 700.

Figure 15:
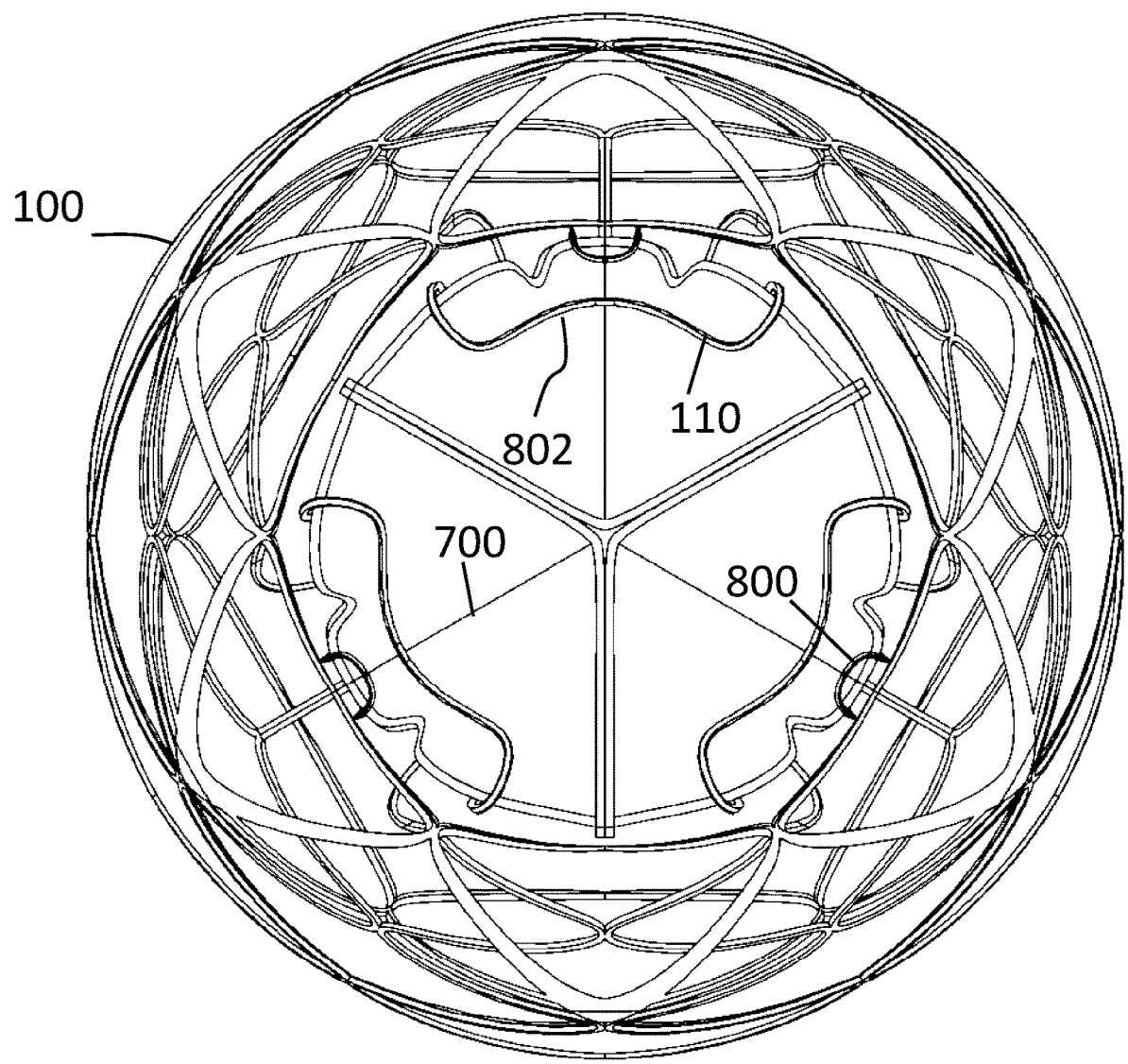
FIG. 15 is a bottom-view illustration of the atrial cage, depicting the atrial cage and corresponding interlock as connected with a valve according to various embodiments of the present invention.
Figure 16A:
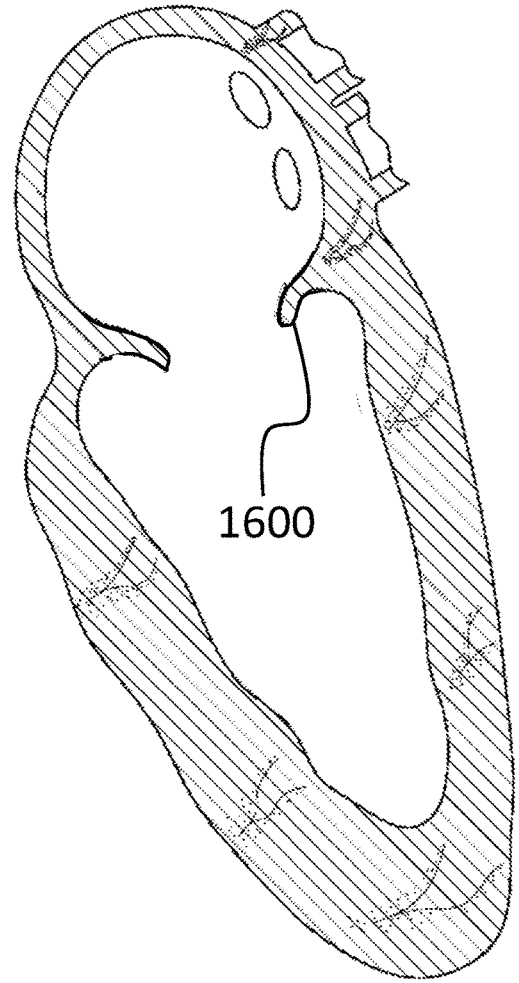
FIG. 16A is an interior-view illustration of a heart chamber, depicting a native mitral valve annulus.
Figure 16B:
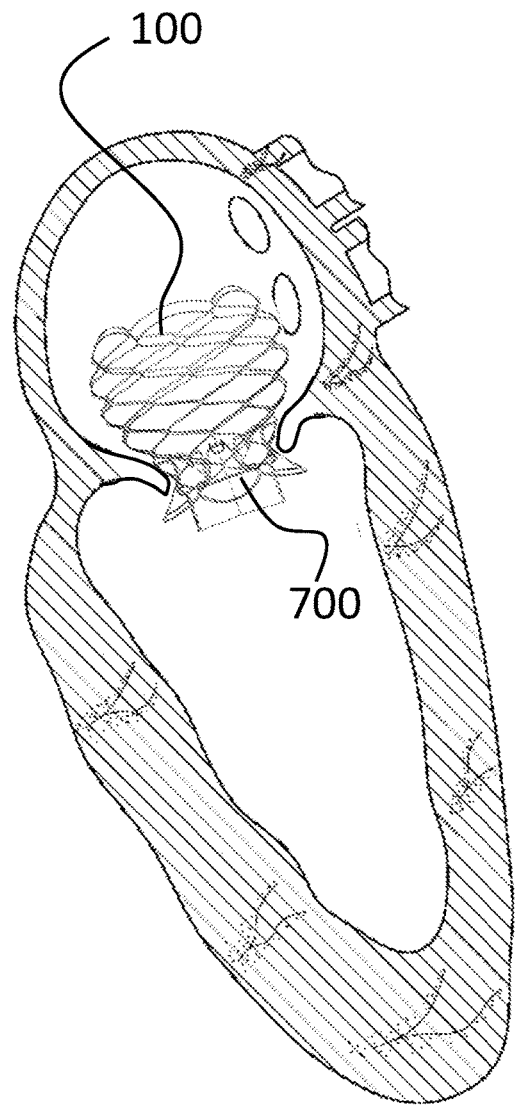
FIG. 16B is an interior-view illustration of the heart chamber, depicting the atrial cage and a bioprosthetic mitral valve as attached with the native mitral valve according to various embodiments of the present invention.

This aspect is further illustrated in FIGS. 10 through 15, which provide front, rear, left, right, top and bottom-view illustrations, respectively, of the atrial cage 100 and corresponding interlock 110 as connected with a valve 700. Notably, the tip clasp 800 can be seen in most figures, while the base clasp 802 is best seen in FIG. 15.

As noted above, the atrial cage 100 is collapsible (as shown in FIGS. 18A and 18B and expandable (as shown in FIGS. 1 through 6 and 8A through 16B). The cage 100 can be collapsed along with an attached valve (as shown in FIG. 18B) so that it can be delivered using any suitable transcatheter delivery device. A non-limiting example of a suitable delivery device is disclosed in U.S. patent application Ser. No. 15/627,360, filed on Jun. 19, 2017 and published as U.S. Patent Publication No. 2017-0360557, entitled, "Delivery System for Percutaneous Delivery And Implantation Of Atrioventricular Heart Valves," the entirety of which are incorporated herein by reference. Due to its wireframe construction and shape, the cage 100 can be collapsed to allow for secure placement via transcatheter delivery and deployment, including by transfemoral, transaortic, transapical, or trans-septal access. During transfemoral, transaortic, and transapical access, the cage 100 is deployed in the atrium prior to deployment of the AV valve. In another aspect, during trans-septal access, the AV valve is deployed prior to the cage 100 being deployed. Once in the desired location, the cage 100 can be expanded using any suitable mechanism, technique or device. In one embodiment, the cage 100 is self-expandable. The cage 100 can self-expand by using a shape memory material such as Nitinol or any other suitable self-expanding material (as an example, the cage can be formed of Nitinol wire or other suitable material or forms). As a non-limiting example, the cage 100 can be shape set in the expanded form such that when delivered and released from a delivery device the cage 100 self-expands. In another embodiment, the cage is balloon-expandable. In one embodiment, the cage 100 is securely attached to the AV valve prosthesis before delivery to the atrium over the transcatheter delivery system. In another embodiment, the cage 100 is delivered separately to the atrium and the prosthetic AV valve is subsequently deployed and attached or interlocked to the cage. In yet another embodiment, the cage 100 can be laser-cut from a tube.

Figure 19A:
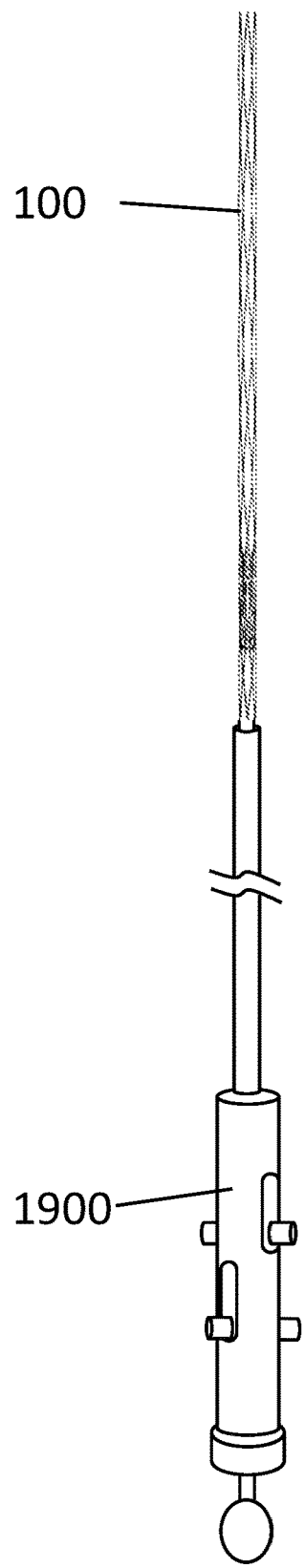
FIG. 19A is a side-view illustration of a delivery device for transcatheter delivery depicting the atrial cage of FIG. 18A without the valve as being positioned over the catheter for percutaneous delivery.
Figure 19B:
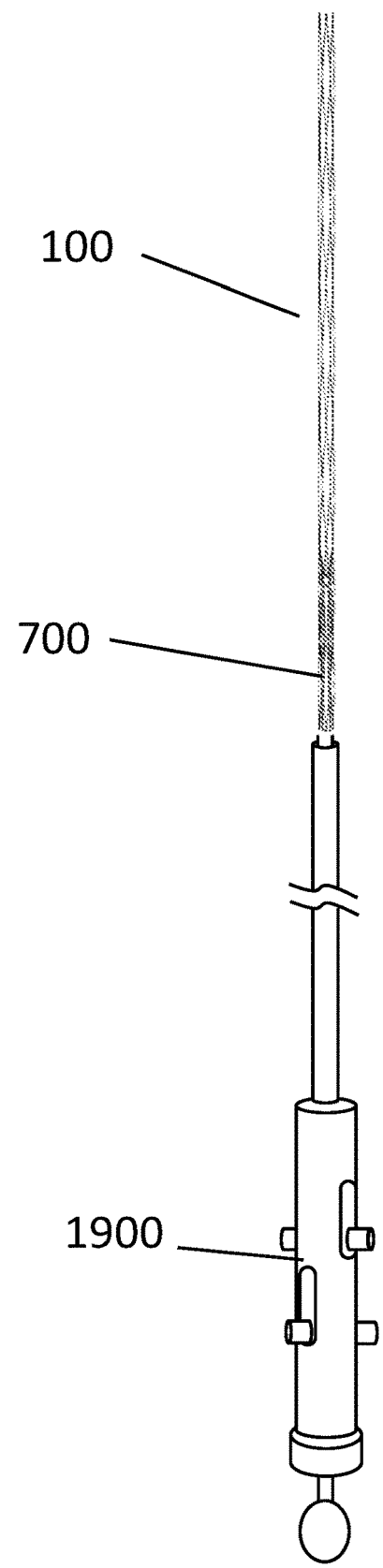
FIG. 19B is a side-view illustration of a delivery device for transcatheter delivery depicting the atrial cage of FIG. 18B with the valve as being positioned over the catheter for percutaneous delivery.

For example and further understanding, FIG. 18A provides a side-view illustration depicting the atrial cage 100 in a collapsed configuration without a valve prosthesis therein, while FIG. 18B depicts the atrial cage 100 in the collapsed configuration with the valve prosthesis 700 positioned the atrial cage 100. As such and as can be appreciated by those skilled in the art, the cage 100 is collapsible over a delivery catheter and is deplorable either separately to have a valve being attached to it consequently or collapsed along with a transcatheter valve 700 already attached to it and both are collapsed over a delivery catheter. This is further illustrated in FIGS. 19A and 19B. FIG. 19A is a side-view illustration of a delivery device 1900 for transcatheter delivery depicting the atrial cage 100 of FIG. 18A without the valve as being positioned over the catheter for percutaneous delivery, while FIG. 19B is a side-view illustration of the delivery device 1900 depicting the atrial cage 100 of FIG. 18B with the valve 700 therein as being positioned over the catheter for percutaneous delivery. As noted above, any suitable delivery device can be employed to deliver the atrial cage and/or valve in accordance with various embodiments of the present invention, a non-limiting example of which includes the delivery device as described in U.S. Patent Publication No. 2017-0360557 and as referenced above. As such, this disclosure is also directed to a method for delivery using such a delivery device.

In other embodiments, the cage 100 is comprised in whole or part of a dissolvable material that is bioabsorbable, bioresorbable, biodegradable, or naturally-dissolving, where the cage may gradually resorb or dissolve away after some time period and after the AV valve prosthesis becomes secured to the AV juncture through natural or artificial processes. Non-limiting examples of such bioabsorbable, bioresorbable, biodegradable, or naturally-dissolving material(s) include base materials that are either metals or polymers, such as iron, magnesium, zinc and their alloys, a poly(L-lactide) polymer similar to that in dissolvable stitches, a drug-eluting material, a mixture of poly-D, L-lactide (PDLLA) and everolimus, markers, such as a pair of radio-opaque platinum markers that allow the device to be visualized during angiography, etc.

In one embodiment, the cage 100 is sized and shaped according to medical imaging means to fit or conform with atrial anatomy to facilitate orientation and positioning of the cage as well as to facilitate orientation and positioning of the attached or to be attached AV valve. For example, using magnetic resonance imaging or other imaging technologies, the shape of a patient's atrium and ventricle can be determined to allow a manufacturer to customize the shape of the cage 100 to match that of the patient's anatomy.

In one embodiment, the cage 100 is custom-sized and shaped to fit a specific patient's anatomy including incorporating some means of 3D scanning. In yet another aspect, the cage 100 is produced by some means of 3D printing.

In one embodiment, the cage 100 is sized and shaped such that once deployed and expanded, at least a part of the cage 100 is in contact with the atrial wall (e.g. where the cage is sized and shaped to match the atrial cavity), or the cage 100 can be formed such that some areas of the cage 100 may be in contact with the atrial wall and some areas of the cage 100 may not be (e.g., where the cage 100 is sized and shaped to anchor the AV valve prosthesis to the AV juncture while avoiding unnecessary contact with select areas of the atrial wall).

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. An atrial cage for placement, securing and anchoring of a prosthetic atrioventricular valve, the atrial cage comprising:
    an atrial component designed to reside within an atrium;
    a valve juncture component connected to the atrial component;
    a ventricular component connected to the valve juncture component, the ventricular component being designed to reside within a ventricle; and
    a first wireform locking mechanism integrally formed within the atrial component such that the first wireform component is a first three-dimensionally spatially curved clasp having a folded U-shape with a first open end, where the first open end of the folded U-shape faces toward the ventricular component, the folded U-shape being adapted to wrap around a portion of the prosthetic atrioventricular valve to lock the prosthetic atrioventricular valve within the atrial cage.

2. The atrial cage as set forth in claim 1, further comprising a second wireform locking mechanism connected to the valve juncture component and projecting inward within the atrial cage, the second wireform locking mechanism being a second three-dimensionally spatially curved clasp having a second folded U-shape with a second open end facing toward an interior of the atrial cage, the second open end of the second folded U-shape being adapted to at least partially wrap around a base of a catch of the prosthetic atrioventricular valve.

3. The atrial cage as set forth in claim 1, wherein the atrial cage is collapsible and expandable, such that when expanded, each of the atrial component, ventricular component and valve juncture component have a diameter such that the diameter of the atrial component and ventricular component is greater than the diameter of the valve juncture component.

4. The atrial cage as set forth in claim 1, wherein the atrial cage is a wireform cage.

5. The atrial cage as set forth in claim 1, wherein the atrial cage is laser-cut from a tube.

6. The atrial cage as set forth in claim 1, wherein the atrial cage is wireform cage formed from Nitinol wire.

7. The atrial cage as set forth in claim 1, wherein the atrial cage is self-expandable.

8. The atrial cage as set forth in claim 1, wherein the atrial cage is balloon-expandable.

9. The atrial cage as set forth in claim 1, wherein the atrial cage is formed in whole or part of a dissolving material, whereby upon implantation within a patient, the atrial cage gradually dissolves away after a designated time period.

10. The atrial cage as set forth in claim 1, wherein the atrial cage is sized and shaped according to medical imaging to fit or conform with atrial anatomy of a subject.

11. The atrial cage as set forth in claim 1, wherein the atrial cage is formed to be deployed and expanded at an atrioventricular juncture, with the atrial cage being sized and shaped such that once deployed and expanded at the atrioventricular juncture, at least a part of the atrial cage is in contact with an atrial wall within the atrium.

12. The atrial cage as set forth in claim 1, wherein the atrial cage is sized and shaped based on three-dimensional scanning of a subject's native atrium and ventricle.

13. The atrial cage as set forth in claim 1, wherein the atrial cage is formed by three-dimensional printing.

14. The atrial cage as set forth in claim 1, wherein the atrial cage is collapsible over a catheter for percutaneous delivery, and independently deployable for subsequent delivery and attachment of a prosthetic valve.

* * * * *